United States Patent
Joseph et al.

(10) Patent No.: US 11,890,209 B2
(45) Date of Patent: Feb. 6, 2024

(54) FLEXIBLE INNER SOCKET FOR PROVIDING INNER CIRCUMFERENCE REDUCTION TO RIGID PROSTHETIC SOCKET

(71) Applicant: Medical Creations, Inc., Aspen, CO (US)

(72) Inventors: Mark C. Joseph, Aspen, CO (US); Sean D. Smith, Denver, CO (US)

( * ) Notice: Subject to any disclaimer, the term of this patent is extended or adjusted under 35 U.S.C. 154(b) by 126 days.

(21) Appl. No.: 16/897,425

(22) Filed: Jun. 10, 2020

(65) Prior Publication Data
US 2021/0386565 A1    Dec. 16, 2021

(51) Int. Cl.
*A61F 2/80*    (2006.01)
*A61F 2/76*    (2006.01)
(Continued)

(52) U.S. Cl.
CPC .......... *A61F 2/7843* (2013.01); *A61F 2/5046* (2013.01); *A61F 2/7812* (2013.01); *A61F 2/80* (2013.01); *B29C 49/06* (2013.01); *B33Y 70/00* (2014.12); *B33Y 80/00* (2014.12); *A61F 2002/501* (2013.01);
(Continued)

(58) Field of Classification Search
None
See application file for complete search history.

(56) References Cited

U.S. PATENT DOCUMENTS

| | | |
|---|---|---|
| 4,019,505 A | 4/1977 | Wartman |
| 4,704,129 A | 11/1987 | Massey |

(Continued)

FOREIGN PATENT DOCUMENTS

| | | | |
|---|---|---|---|
| EP | 1112727 A1 | 7/2001 | |
| FR | 3 061 852 A1 * | 7/2018 | ............... A61F 2/78 |

(Continued)

OTHER PUBLICATIONS

Bracken S., "Graduate Student Works to Make Prosthetics Accessible in Developing Countries," PennState News, Feb. 2, 2016, 5 pages, https://news.psu.edu/story/390530/2016/02/02/academics/graduate-student-works-make-prosthetics-accessible-developing.

(Continued)

*Primary Examiner* — David H Willse
(74) *Attorney, Agent, or Firm* — Messner Reeves LLP; Scott J. Hawranek

(57) ABSTRACT

A flexible inner socket is fabricated by forming a pre-socket. The pre-socket includes a body formed with an opening and an enclosed end. The enclosed end is opposite to the opening. The body of the pre-socket has an outer circumference that is smaller than the inner circumference of the rigid prosthetic socket. Different portions of the body may have different thicknesses. The preform socket is heated. After the heating, the flexible inner socket is formed by molding the pre-socket onto the inner surface of the rigid prosthetic socket to form the flexible inner socket. The inner circumference of the rigid prosthetic socket is reduced by a thickness of the flexible inner socket when the flexible inner socket is attached to the inner surface of the rigid prosthetic socket. An opening of the flexible inner socket may be trimmed after the formation to fit contours of an opening of the rigid prosthetic socket.

29 Claims, 13 Drawing Sheets

(51) Int. Cl.
    *A61F 2/78*     (2006.01)
    *A61F 2/50*     (2006.01)
    *B29C 49/06*     (2006.01)
    *B33Y 70/00*     (2020.01)
    *B33Y 80/00*     (2015.01)

(52) U.S. Cl.
    CPC ............... *A61F 2002/5052* (2013.01); *A61F 2002/5053* (2013.01); *A61F 2002/5056* (2013.01); *A61F 2002/7605* (2013.01); *A61F 2002/785* (2013.01); *A61F 2002/805* (2013.01)

(56) References Cited

U.S. PATENT DOCUMENTS

| | | | |
|---|---|---|---|
| D336,519 S | 6/1993 | Greene et al. | |
| 5,376,127 A | 12/1994 | Swanson | |
| 5,824,111 A | 10/1998 | Schall et al. | |
| 5,885,509 A | 3/1999 | Kristinsson | |
| 5,980,803 A | 11/1999 | Slemker et al. | |
| D429,335 S | 8/2000 | Caspers et al. | |
| 6,287,345 B1 | 9/2001 | Slemker et al. | |
| D456,900 S | 5/2002 | Daftary | |
| D462,768 S | 9/2002 | Meyer et al. | |
| 6,444,282 B1 | 9/2002 | Shirer | |
| D477,875 S | 7/2003 | Meyer et al. | |
| D499,487 S | 12/2004 | Bedard et al. | |
| 6,869,560 B1 | 3/2005 | Drouin et al. | |
| 6,991,444 B1* | 1/2006 | Laghi ................... | A61F 2/5044 |
| | | | 425/389 |
| 8,303,527 B2 | 11/2012 | Joseph | |
| 8,528,796 B1 | 9/2013 | Bosko et al. | |
| D748,791 S | 2/2016 | Kampas et al. | |
| D748,792 S | 2/2016 | Kampas et al. | |
| D778,452 S | 2/2017 | Cespedes et al. | |
| 9,635,967 B1 | 5/2017 | Hopper | |
| D798,453 S | 9/2017 | Cheng et al. | |
| 2005/0240282 A1 | 10/2005 | Rush et al. | |
| 2005/0267600 A1 | 12/2005 | Haberman et al. | |
| 2006/0161267 A1 | 7/2006 | Clausen | |
| 2007/0055383 A1 | 3/2007 | King | |
| 2008/0004716 A1 | 1/2008 | Hoerner | |
| 2008/0161939 A1 | 7/2008 | Perkins | |
| 2008/0188948 A1 | 8/2008 | Flatt | |
| 2008/0234836 A1 | 9/2008 | Taylor | |
| 2008/0269914 A1 | 10/2008 | Coppens et al. | |
| 2011/0320010 A1 | 12/2011 | Vo | |
| 2013/0123940 A1 | 5/2013 | Hurley et al. | |
| 2014/0025183 A1 | 1/2014 | Kelley et al. | |
| 2014/0149082 A1* | 5/2014 | Sanders ................ | A61F 2/5046 |
| | | | 703/1 |
| 2014/0207253 A1 | 7/2014 | Horton et al. | |
| 2015/0265434 A1 | 9/2015 | Hurley et al. | |
| 2015/0289998 A1* | 10/2015 | Chabloz ................ | B29C 51/002 |
| | | | 264/129 |
| 2016/0143752 A1 | 5/2016 | Hurley et al. | |
| 2016/0228266 A1 | 8/2016 | Alley | |
| 2019/0053917 A1 | 2/2019 | Mosler | |

FOREIGN PATENT DOCUMENTS

| | | |
|---|---|---|
| WO | 2014035561 A1 | 3/2014 |
| WO | 2014182537 A1 | 11/2014 |
| WO | 2017144604 A1 | 8/2017 |

OTHER PUBLICATIONS

Dupere, K., "The 12 Most limpressive Social Good Innovations from June," Mashable, Jul. 1, 2016, 10 pages, [Online] [Retrieved on Aug. 20, 2019],URL: https://mashable.com/2016/07/01/social-good-innovations-june-2016.

International Search report and Written Opinion issued in International Application No. PCT/US2019/020484, dated Jun. 7, 2019, 12 pages.

International Preliminary Report issued in Application No. PCT/US2019/020484, dated Sep. 17, 2020, 11 pages.

Kemp, T., "Affordable, Adjustable Socket in the Works for Amputees in Need," O&P News, Jun. 1, 2016, 5 pages, [Online] [Retrieved on Aug. 20, 2019] URL: http://oandpnews.org/2016/06/01/affordable-adjustable-socket-in-the-works- -for-amputees-in-need/>.

Wilson Jr., A.B., "A Material for Direct Forming of Prosthetic Sockets," Artificial Limbs, 1970, vol. 14 (1), pp. 53-56.

Zhe., et al., U.S. Appl. No. 61/820,233, filed May 7, 2013.

Extended European Search Report issued in European Application No. 20190765111, dated Jan. 12, 2022, 11 pages.

Supplementary European Search Report issued in European Application No. EP20939831.2 dated Feb. 6, 2023, 7 pages.

Willowood, "2018 Product Catalog," Oct. 2017, 172 pages.

Manufacturing Guidelines. "Prosthetics-Orthotics Thermoforming Polypropylene (Draping Technique)," Physical Rehabilitation Programme, International Committee of the Red Cross, 2015, 20 pages.

* cited by examiner

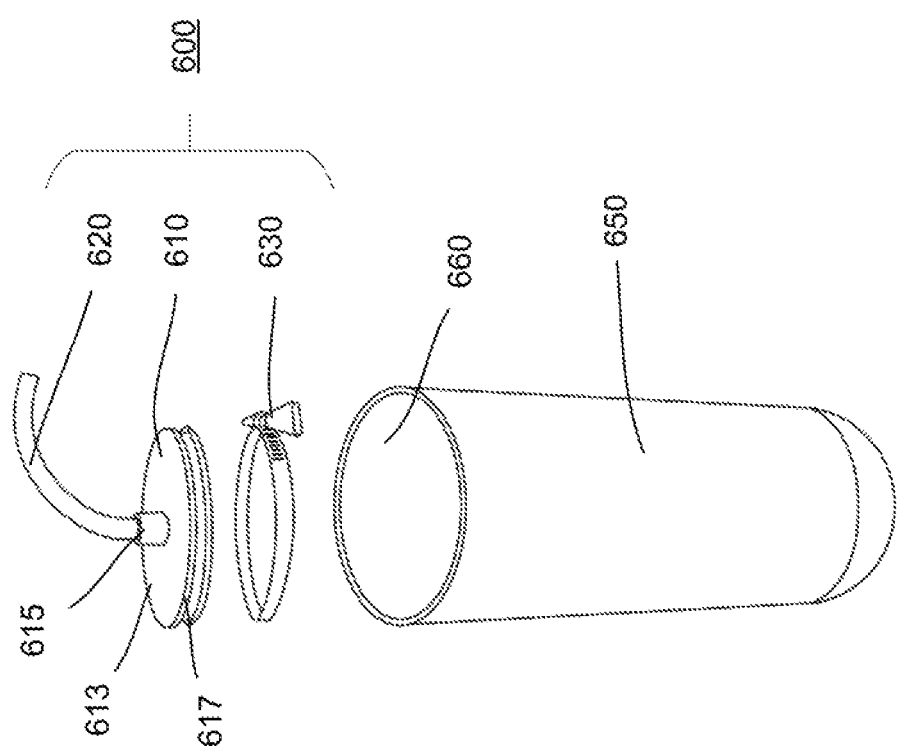

FLEXIBLE INNER SOCKET FOR PROVIDING INNER CIRCUMFERENCE REDUCTION TO RIGID PROSTHETIC SOCKET

BACKGROUND OF THE INVENTION

Field of the Disclosure

The present disclosure generally relates to a flexible inner socket that can be placed within a prosthetic socket, method of using and making the same and more particularly to flexible inner socket for providing at least a partial inner circumference reduction of the prosthetic socket.

Description of the Related Arts

Global interior circumference reduction (also referred to as "global reduction") of rigid prosthetic sockets is required to provide a tight fit to the residual limb so as to bear weight on the compressed soft tissue thereby reducing loads to the amputated bone ends. The related art process of applying global reduction to rigid prosthetic sockets is an artful manual process.

Conventionally, a practitioner manually forms a rigid prosthetic socket over a plaster model of a user's residual limb. The practitioner first manually forms the plaster model from a cast of the user's residual limb. After the plaster model is formed, the practitioner reduces the circumference of the plaster model by hand crafting, e.g., hand scraping and hand sanding. As the rigid prosthetic socket is formed over the globally reduced plaster model, the reduction in the circumference of the plaster model causes the global reduction of the rigid prosthetic socket.

Sometimes, a flexible inner socket is placed inside the rigid prosthetic sockets for cushioning, comfort, and adjustability. In the conventional process, the practitioner manually forms the flexible inner socket over the globally reduced plaster model, and then forms the rigid prosthetic socket over the flexible inner socket. However, the conventional process of making flexible inner sockets is time consuming, produces a large amount of waste, and has a high failure rate. Practitioners have to manually make flexible inner sockets one by one by hand draping hot thermoformable sheet plastic over plaster models. And they often have to repeat the process multiple times to get a satisfactory flexible inner socket. Because the plaster model, the flexible inner socket, and the rigid prosthetic socket are all made manually by the practitioner, the conventional process of applying the global reduction to the rigid prosthetic socket requires a high degree of practice and experience. Due to the challenge of this artful manual process, lack of practice and experience of practitioners, and intra- and inter-practitioner variability, conventionally applied global reduction is often inaccurate, which can cause discomfort to the user regardless of the use of the flexible inner socket. Thus, improved techniques for applying global reduction to rigid prosthetic sockets and for forming flexible inner sockets are needed.

SUMMARY OF THE INVENTION

Accordingly, the invention is directed towards a flexible inner socket for providing inner circumference reduction to prosthetic socket.

An advantage of the invention is to provide a process that is reproducible and faster than related art processes.

Another advantage of the invention is to provide accurate and precise global reduction of the fit of a prosthetic socket that is based on the thickness of the flexible inner socket instead of the common laborious practice in the art of hand scraping, grinding and sanding and the like.

Yet another advantage of the invention is to provide flexible inner sockets in varied thicknesses that can precisely reduce the global reduction of the fit as the user's limb changes size during the day.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, relate to a flexible inner socket design and process of fabricating a flexible inner socket. The flexible inner socket is formed on an inner surface of a prosthetic socket that has previously been formed to fit a residual limb of a user. The prosthetic socket was formed either directly over the residual limb of the user or over a model of the residual limb that has a shape matching the anatomical shape of at least a portion of the residual limb. Accordingly, the inner surface of the prosthetic socket has a contour and dimensions that match the anatomical shape of at least a portion of the residual limb. Zero or insufficient global reduction has been applied to the rigid prosthetic socket, or the residual limb has shrunk to the extent that the original global reduction is no longer effective. The flexible inner socket, when attached to the inner surface of the rigid prosthetic socket, adds additional thickness to the prosthetic socket so that the resulting device (i.e., the prosthetic socket plus the flexible inner socket) has a reduced inner circumference. This is referred to as global interior circumference reduction or global reduction of the prosthetic socket. The global reduction can be precisely controlled based on the thickness of the flexible inner socket.

In another aspect of the invention, an embodiment is directed towards a flexible inner socket is made using a preformed socket (also referred to as "pre-socket"). The pre-socket is formed from a material, e.g., polymer, thermoplastic material, and the like, using techniques such as injection molding, rotational molding, three-dimensional (3D) printing, blow molding, combinations of the same and the like. The pre-socket has an opening (e.g., the opening through which the residual limb will ultimately be inserted) and an enclosed end (e.g., where the residual limb ultimately rests). The enclosed end is opposite the opening. The pre-socket has an outer circumference that is smaller than the inner circumference of the rigid prosthetic socket. The pre-socket is heated and then molded onto the inner surface of the rigid prosthetic socket to form the flexible inner socket. In another aspect of the invention, an embodiment is directed towards a method of forming a flexible inner socket including providing a rigid prosthetic socket configured to fit at least a portion of a residual limb of a user. The rigid prosthetic socket comprises a first end, a second end, an inner circumference, the first end having an opening, the second end being substantially closed, and an inner surface having contours that substantially mimic contours of the residual limb. The rigid prosthetic socket has not been globally reduced in dimension. The method also includes providing a flexible pre-socket comprising a thermoformable material. The flexible pre-socket includes a first end, a second end, a thickness, an inner circumference, and an outer circumference, the first end having an opening, and the second end being substantially closed. The method further includes heating the thermoformable material of the flexible pre-socket to a temperature so that the flexible pre-socket becomes a formable flexible pre-socket and arranging at least a portion of the formable flexible pre-socket into the rigid prosthetic socket. Next the heated pre-socket is molded onto the inner surface of the rigid prosthetic socket such that the outer circumference of the formable flexible pre-socket substantially follows the contours of the inner surface of the rigid prosthetic socket, thereby reducing the inner circumference of the rigid prosthetic socket in a predetermined manner based on the thickness of the flexible pre-socket to provide a globally reduced fit of the rigid prosthetic socket.

Yet in another aspect of the invention, an embodiment is directed towards a method of forming a flexible inner socket including providing a rigid prosthetic socket configured to fit at least a portion of a residual limb of a user. The rigid prosthetic socket includes a first end, a second end, an inner circumference, the first end having an opening, the second end being substantially closed, and an inner surface having contours that substantially mimic contours of the residual limb, and the rigid prosthetic socket has not been globally reduced in dimension. The method also includes providing a flexible pre-socket and heating the flexible pre-socket to a temperature so that the flexible pre-socket becomes a moldable. The heated pre-socket is then arranged into the rigid prosthetic socket. Next, the heated pre-socket is molded onto the inner surface of the rigid prosthetic socket such that the outer circumference of the formable flexible pre-socket substantially follows the contours of the inner surface of the rigid prosthetic socket.

In still another aspect of the invention, an embodiment is directed towards a method of forming a flexible inner socket. The method includes providing a prosthetic socket having an inner surface with contours that substantially mimic contours of the residual limb and providing a pre-socket. The pre-socket is heated with a heat source to a temperature where the pre-socket becomes a moldable and at least a portion of the pre-socket is arranged into the prosthetic socket. Next, the heated pre-socket is molded onto the inner surface of the rigid prosthetic socket such that an outer circumference of the pre-socket substantially follows one or more of the contours of the inner surface of the rigid prosthetic socket.

Yet still another aspect of the invention, an embodiment is directed towards a prosthetic system for an end user. The system includes a rigid prosthetic socket configured to fit at least a portion of a residual limb of a user. The rigid prosthetic socket includes a first end, a second end, an inner circumference, the first end having an opening, the second end being closed, and an inner surface having contours that substantially mimic contours of the residual limb and the rigid prosthetic socket has not been globally reduced in dimension. The system further includes a molded flexible pre-socket comprising a thermoformable material, wherein the flexible pre-socket comprises a first end, a second end, a thickness, an inner circumference, and an outer circumference, the first end having an opening, and the second end being closed. The molded flexible pre-socket substantially follows the contours of the inner surface of the rigid prosthetic socket, thereby reducing the inner circumference of the rigid prosthetic socket in a predetermined manner based on the thickness of the flexible pre-socket to provide a globally reduced fit of the rigid prosthetic socket.

Yet still another aspect of the invention, an embodiment is directed towards a prosthetic system for an end user. The air inlet assembly for use with a flexible pre-socket includes a sealing mechanism, a lid having a first side, a second side, a valve and a channel region around a circumference of the lid, the channel region configured to receive the sealing mechanism and at least a portion of the flexible pre-socket. The air inlet assembly further includes a hose configured to be releasably connected to the valve and the lid is configured to cover an opening on the flexible pre-socket and the sealing mechanism is configured to seal the lid to the flexible pre-socket. Unlike conventional methods of fabrication where the flexible inner socket is formed on a plaster cast of the limb and where the rigid prosthetic socket is formed over the flexible inner socket, the flexible inner socket and method of fabricating described here include actually forming the flexible inner socket inside the rigid prosthetic socket, where the prosthetic socket was previously formed to fit the user's residual limb, without global reduction being applied. Also, the flexible inner socket is formed from a preformed socket that can be made by using techniques such as injection molding, rotational molding, 3D printing, blow molding, combinations of the same and the like, as opposed to hand crafting in the conventional methods. Thus, the inner circumference reduction provided by the flexible inner socket here can be more accurate and precise. The techniques can be used to manufacture pre-sockets of various shapes and sizes to fit rigid prosthetic sockets of various shapes and sizes.

This Summary section is neither intended to be, nor should be, construed as being representative of the full extent and scope of the present disclosure. Additional benefits, features and embodiments of the present disclosure are set forth in the attached figures and in the description hereinbelow, and as described by the claims. Accordingly, it should be understood that this Summary section may not contain all of the aspects and embodiments claimed herein.

Additionally, the disclosure herein is not meant to be limiting or restrictive in any manner. Moreover, the present disclosure is intended to provide an understanding to those of ordinary skill in the art of one or more representative embodiments supporting the claims. Thus, it is important that the claims be regarded as having a scope including constructions of various features of the present disclosure insofar as they do not depart from the scope of the methods and apparatuses consistent with the present disclosure (including the originally filed claims). Moreover, the present disclosure is intended to encompass and include obvious improvements and modifications of the present disclosure.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 6 illustrates an air inlet assembly used for molding a preformed socket, in accordance with another embodiment;

DETAILED DESCRIPTION

Figure 1C:
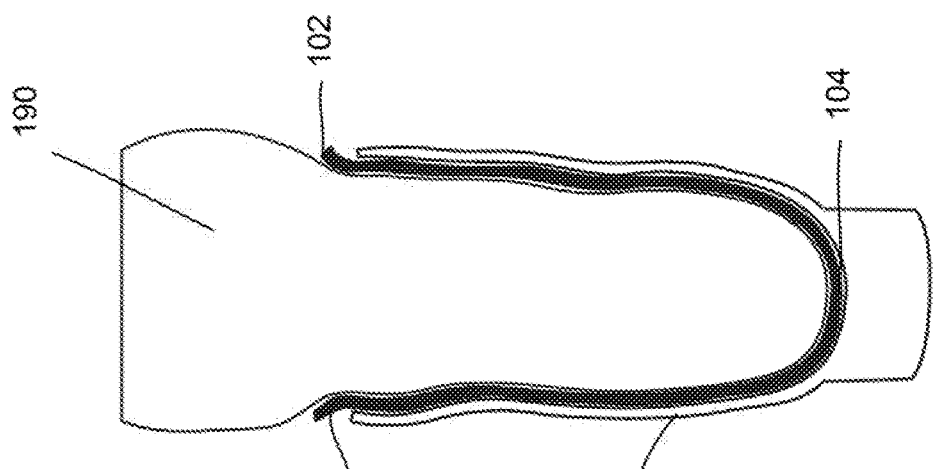
FIG. 1C illustrates a cross-sectional view of a residual limb of a user at least partially arranged in the flexible inner socket and the prosthetic socket of FIGS. 1A-1B, in accordance with the embodiment.

In the following description of embodiments, numerous specific details are set forth in order to provide more thorough understanding. However, note that the embodiments may be practiced without one or more of these specific details. In other instances, well-known features have not been described in detail to avoid unnecessarily complicating the description.

Embodiments are described herein with reference to the figures where like reference numbers indicate identical or functionally similar elements. Also, in the figures, the left most digits of each reference number correspond to the figure in which the reference number is first used.

One embodiment relates to forming a flexible inner socket including the steps of providing a prosthetic socket configured to fit at least a portion of a residual limb of a user. The prosthetic socket includes a first end, a second end, an inner circumference, and an inner surface having contours that substantially match contours of the residual limb, wherein the prosthetic socket has not been globally reduced in dimension, was insufficiently globally reduced, or changes in the patient's residual limb have resulted in the global reduction to be insufficient. The process also includes forming a pre-socket by using a thermoformable material, the pre-socket comprising a first end, a second end, a thickness, an inner circumference, and an outer circumference, the first end having an opening, and the second end being closed. The process further includes heating the thermoformable material of the pre-socket to a temperature so that the pre-socket becomes a formable pre-socket arranging the formable pre-socket into the prosthetic socket. The process also includes molding the formable pre-socket onto the inner surface of the prosthetic socket such that the outer circumference of the formable pre-socket substantially follows the contours of the inner surface of the prosthetic socket, thereby reducing the inner circumference of the prosthetic socket in a predetermined manner based on the thickness of the pre-socket to provide a globally reduced fit of the prosthetic socket.

The term pre-socket and socket are used interchangeably herein.

Formable pre-socket or socket means a thermoplastic or thermoformable material that when heated, becomes pliable and stretchable so as to assume a new shape when formed and thereby holding that shape when cooled. In one embodiment, the heating temperature is between about 170° F. to about 300° F. and the temperature when cooled is about 125° F. or below. In a preferred embodiment, the heating temperature is 225° F. to about 280° F. (and when cooled about 150° F. or below).

In one embodiment, the pre-socket may have an open end and a substantially closed end. The substantially closed end may have a channel that extends from an inside portion to an outside portion through a thickness of the pre-socket.

In one embodiment, the preformed socket is heated, e.g., to a temperature in a range from about 190° F. to about 285° F. or greater to become pliable, and molded onto the inner surface of the rigid prosthetic socket. In a preferred embodiment, the preformed socket is placed heated, e.g., to a temperature in a range from about 170° F. and 280° F. The pre-socket can be heated with a heat source, e.g., an infrared heater, convection oven, silicone pad heater, halogen tube heater or other common heating devices.

Globally reduced means a reduction in the inner circumference of a lower leg prosthetic socket that is applied over the majority of the interior so that a user's residual limb soft-tissue is compressed in a conical fashion when worn so as to properly bear weight away from the amputated bone end. Global reduction is typically applied by hand filing, scraping and sanding of the plaster model which is an imprecise method. Global reduction is a common industry term well known and the typical reduction is about 4%.

In one embodiment, the thickness of the pre-socket is determined based on the inner circumference of the prosthetic socket so as to achieve a desired global reduction according to Formula 1:

$$T = C/(2 \cdot \pi) \cdot X/100 \quad \text{(Formula 1)}$$

The units and variables are as follows: T is thickness of the pre-socket [mm], C is inner circumference of the rigid prosthetic socket that has not been globally reduced in dimension [mm], and X is global reduction %.

In one embodiment, the pre-socket of the flexible inner socket becomes the final flexible inner socket after it is molded as described herein.

In one embodiment, the thickness of the flexible inner socket can be controlled in the fabrication process (such as a manufacturing process), e.g., by controlling the thickness of the preformed socket from which the flexible inner socket is formed. The preformed socket may have a uniform thickness, or different portions of the preformed socket can have different thicknesses. Accordingly, compression of the tissue of the user's residual limb can be precisely and selectively controlled to achieve proper distribution of the weight of the user and comfortable fit of the prosthetic socket. Compared with conventional processes of fabricating flexible inner sockets one by one by hand, this two-step process is more repeatable and less dependent on intra- and inter-practitioner variability in hand-shaping plaster models and rigid prosthetic sockets. It also requires less skill, guesswork, material waste, and time. Also, this two-step process allows for mass manufacturing of the flexible inner socket.

In one embodiment, the pre-socket or socket can be formed with blow molding, injection material or other techniques. In one embodiment, the pre-socket or socket is formed from a thermoformable material. The thermoformable material includes one or more of a thermoplastic elastomer material, a thermoplastic polyurethane (TPU) material, a thermoplastic polyurethane foam material, a thermoplastic vulcanizate (TPV) material, a rubber material, an ultra-low density polyethylene (ULDPE) material, an ethylene vinyl acetate (EVA) material, a styrene material and blends of the same.

In one embodiment, the thermoformable material can include a closed cell foam material, a non-compressible material, or a compressible material.

In one embodiment, the thermoformable material has one or more of the following physical properties: an A-type durometer in a range from about 55 to about 95, an elongation in a range from about 200% to about 600%, and a forming point temperature in a range from about of below about 170° F. to about 300° F.

In one embodiment, the pre-socket is formed with an opening and with an enclosed end that is opposite to the opening. The pre-socket has a circumference determined based on an inner circumference of a prosthetic socket, e.g., the circumference of the pre-socket can be smaller than the inner circumference of the prosthetic socket, e.g., smaller by up to 15%, so that the pre-socket can be arranged on inside the prosthetic socket. The prosthetic socket has previously been formed to fit a residual limb of a user with techniques described herein or conventional techniques. No global reduction has been applied or needed to the prosthetic socket, thereby saving tremendous process time in the overall process.

In one embodiment, the flexible inner socket is formed after a preformed socket is arranged inside the prosthetic socket. The preformed socket is heated, so that is pliable and pressed onto the inner surface of the prosthetic socket such that the outer circumference of the heated preformed socket substantially follows the contours of the inner surface of the prosthetic socket, thereby reducing the inner circumference of the prosthetic socket in a predetermined manner based on the thickness of the pre-socket to provide a globally reduced fit of the prosthetic socket. The preformed socket can be pressed into the prosthetic socket with an assistance of a pressured device, e.g., an airbag can be utilized to press against the inner surface of the heated preformed socket so that it molds against the inner surface of the prosthetic device.

In one embodiment, a method of forming a flexible inner socket, by providing a prosthetic socket configured to fit at least a portion of a residual limb of a user, the prosthetic socket comprises a first end, a second end, an inner circumference, the first end having an opening, the second end being closed, and an inner surface having contours that substantially mimic contours of the residual limb, wherein the prosthetic socket has not been globally reduced in dimension. Next, providing a pre-socket including a thermoformable material, the pre-socket including a first end, a second end, a thickness, an inner circumference, and an outer circumference, the first end having an opening, and the second end being closed. The method further includes heating the thermoformable material of the pre-socket to a temperature so that the pre-socket becomes a formable pre-socket and arranging at least a portion of the formable pre-socket into the prosthetic socket. The method also includes molding the formable pre-socket onto the inner surface of the prosthetic socket such that the outer circumference of the formable pre-socket substantially follows the contours of the inner surface of the prosthetic socket, thereby reducing the inner circumference of the prosthetic socket in a predetermined manner based on the thickness of the pre-socket to provide a globally reduced fit of the prosthetic socket.

Optionally and/or alternatively, the method further includes to assist with the molding providing an air inlet assembly including a lid, a sealing mechanism, a valve in communication with the lid and a hose in communication with the valve. The lid is configured to cover the opening on the formable pre-socket. The sealing mechanism is used to seal the lid to formable pre-socket and the entire assembly is arranged into at least a portion a prosthetic socket. The formable pre-socket is inflated with the air inlet assembly to a pressure configured to conformally arrange at least a portion of an outer surface of the formable pre-socket against an inner surface of the prosthetic socket.

In one embodiment, the flexible inner socket can be attached to the inner surface of the rigid prosthetic socket such that it holds the residual limb when a user wears the prosthetic socket. The flexible inner socket can be designed to be removable or non-removable from the prosthetic socket.

In one embodiment, the thickness of the flexible inner socket is predetermined and configured to provide a globally reduced fit of the prosthetic socket. In one embodiment, the inner circumference reduction of the prosthetic socket allows tissue of the residual limb of the user to be compressed against the material of the flexible inner socket. The compressing of the tissue in this manner more evenly distributes the weight born by the residual limb over the entire residual limb. The compressed tissue bears more weight over a larger surface area instead of bearing much of the weight at various points on the tissue that correspond to the bone ends and prominences of the residual limb. This allows the prosthetic socket to have a tight and comfortable fit.

In one embodiment, a rigid prosthetic socket is sized and fitted to the user's residual limb by various conventional techniques including making a plaster cast and filling the cast with plaster to make a model which the socket is subsequently made from. Optionally, a heat formable material can be directly formed to the plaster model or directly to the user's residual limb. The prosthetic socket would require a global reduction, e.g., about 4%, so that it fits tightly to the residual limb to properly fit and bear weight. In this embodiment, aspects of the invention and methods are configured to omit the global reduction step which is time consuming, requires considerable experience and technique, and often results in an imprecise shape and fit. In this case the socket is fitted precisely to the residual limb without any global reduction.

After the rigid prosthetic socket, which has not been reduced, was insufficiently globally reduced, or, as a result of residual limb volume reduction, provides insufficient global reduction the method of using and making a flexible inner socket is applicable. In this method, a global reduction is achieved by heat forming a pre-socket precisely to an inside of the rigid socket. The pre-socket is made from a material with properties described herein. In one embodiment, the pre-socket becomes softened and formable at about 250° F.

In one embodiment, the pre-socket is premade by injection molding or blow molding in economical repeatable quantities to a shape that fits inside the rigid prosthetic socket. The premade pre-sockets can be made in different sizes so that the proper size is selected that fits closely inside the rigid prosthetic socket yet is taller, so it extends out the proximal end. Also, they can be made in varied thicknesses as well so that the desired amount of global reduction is achieved. In one embodiment, the thickness of the pre-socket is about 2 mm thick and can fit a person with a medium size residual limb, measuring about 32 cm to about 34 cm at the distal end. The thickness after molding as described herein is configured to result in a global reduction, e.g., about 4%. Of course, other thicknesses can be utilized, e.g., according to Formula 1. The pre-socket is molded into a flexible inner socket as described herein. Next it can be marked for trimming so that it extends about 2 cm above the edge of the rigid prosthetic socket. It is removed, trimmed with scissors and the edge is buffed round and smooth with a rotating buffing tool.

Optionally and/or alternatively, after the flexible inner socket is fitted or molded back inside the rigid prosthetic socket, the extending edge can be heated, e.g., about 250° F. with a heat source, e.g., a heat gun, and it can be shaped, e.g., flared by gloved hands to precisely fit the needs of the residual limb. Depending on the suspension system desired to retain the socket onto the limb, a small hole can be cut in the distal end to allow for suction or vacuum air to pass through. Or, a larger hold can be cut to allow for a pin lock system to pass through.

The system or combined socket, e.g., rigid prosthetic socket and flexible inner socket, can be tested for fit by the user. If the fit needs adjustment, heat can be applied with a heat source to the flexible inner socket to reshape it. In a preferred embodiment, the rigid prosthetic socket is also heat formable and adjusted as described with U.S. patent Ser. Nos. 15/914,480 and 16/516,199, both of which are hereby incorporated by reference as if fully set forth herein. In such a case, both the flexible inner socket and rigid prosthetic can be heated and adjusted in shape for a truly customizable fit that can be done at any time. The result is a precisely globally reduced socket that fits to compress the limb properly to bear weight and stay in place which is far superior to the typical hand reduction done to the plaster limb model by the practitioner.

A typical problem for amputees is that their limb can shrink or grow in circumference at different times through the day, week, month, and/or year. This typically occurs as the day passes and use reduces fluid in the limb but it can happen at any time. Additional flexible inner sockets can be made in varied thickness that the user can insert into the rigid prosthetic socket to increase or reduce global reduction. They can replace the original flexible inner socket or be layered up to change the fit. These additional flexible inner sockets can be made in the same fashion described herein.

Optionally and/or alternatively, an embodiment is directed towards a method of forming a flexible inner socket with the use of a cast of the residual limb filled with plaster to create a positive model of the limb. The positive model is globally reduced using traditional grinding and carving techniques. A pre-socket is formed over the globally reduced model, thereby creating a flexible inner socket with an inner surface that matches or mimics the surface and contours of the positive model that has been globally reduced. The pre-socket thickness may be any thickness described herein. The flexible inner socket may be formed with hand pressure or with the aid of vacuum pressure or positive pressure, e.g., with apparatus and techniques described herein. A rigid prosthetic socket is then fabricated over the flexible inner socket so that the inner surface of the rigid socket matches the surface and contours of the outer surface of the flexible inner socket. Use of the pre-socket rather than traditional sheet materials saves processing steps, time and reduces material waste, and the end result is a rigid prosthetic socket with the flexible inner socket that provides global reduction to the limb.

Reference will now be made in detail to an embodiment of the present invention, example of which is illustrated in the accompanying drawings.

Figure 1B:
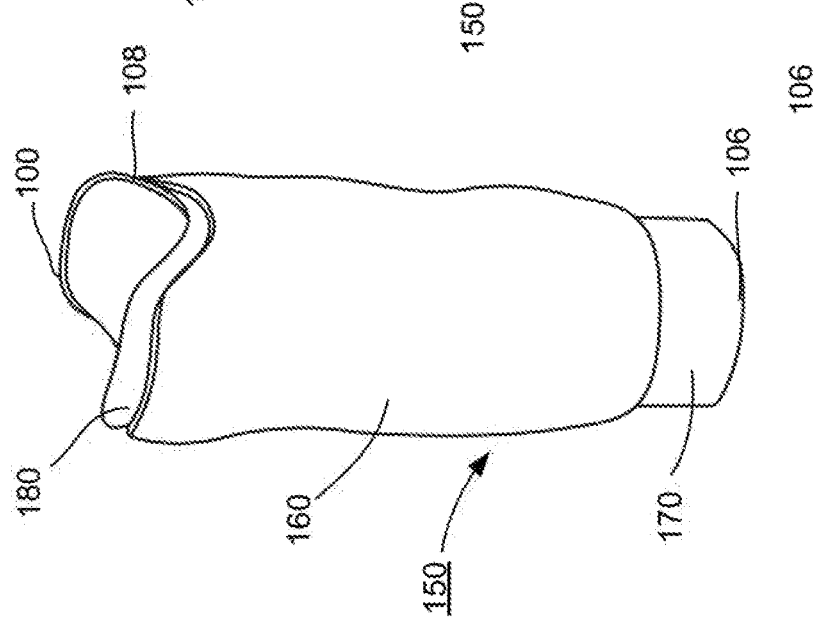
FIG. 1B illustrates the flexible inner socket of FIG. 1A arranged in a prosthetic socket of FIG. 1B, in accordance with the embodiment.
Figure 1A:
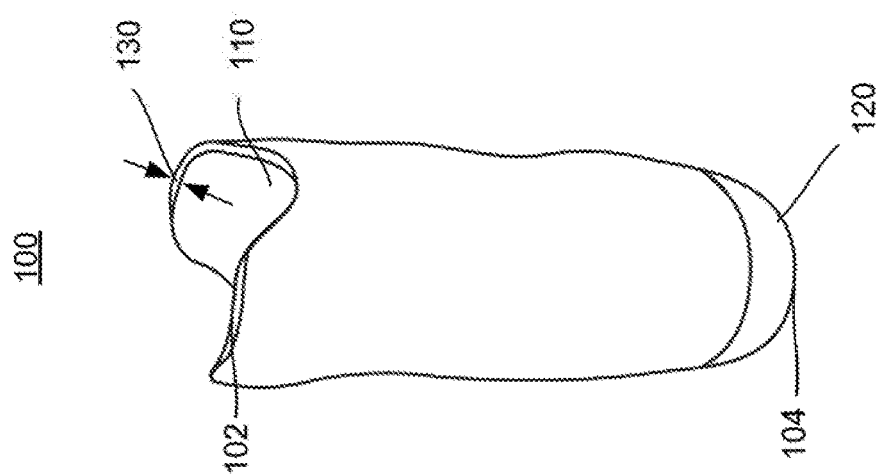
FIG. 1A is a perspective view of a flexible inner socket, in accordance with an embodiment of the invention.

FIG. 1A is a perspective view of a flexible inner socket 100 fabricated from a pre-socket in accordance with an embodiment of the invention. FIG. 1B illustrates the flexible inner socket of FIG. 1A arranged in a prosthetic socket of FIG. 1B, in accordance with the embodiment. FIG. 1C illustrates a residual limb of a user at least partially arranged in the flexible inner socket and the prosthetic socket of FIGS. 1A-1B, in accordance with the embodiment.

Referring to FIGS. 1A-1C, a flexible inner socket formed as described herein is generally depicted with reference to 100 and a prosthetic socket is generally depicted with reference to 150. In a preferred embodiment, the prosthetic socket is rigid having a hardness of greater quantified as an A-type durometer in a range from about 100 or greater.

The flexible inner socket 100 has a first end 102, a second end 104, and the first end 102 has an opening 110 configured and dimensioned to receive at least a portion of a residual limb 190 of a user. The second end 104 is closed end 120 in a rounded type orientation. Optionally and/or alternatively, the second end has a hole or channel that extends through the thickness 130 of the flexible inner socket 100. A cavity or partial channel is formed extending from the open first end 102 to the closed second end 104. The cavity or channel is configured to enclose at least a portion of the residual limb 190. The volume of the cavity is greater than the volume of the residual limb. The flexible inner socket has a thickness 130. In a preferred embodiment the thickness is in a range from about 1 mm to about 8 mm. The thickness may be constant or variable about the x-axis or y-axis of the flexible inner socket. In one embodiment, the prosthetic socket 150 can be formed and is described with reference to U.S. patent Ser. Nos. 15/914,480 and 16/516,199, both of which are hereby incorporated by reference as if fully set forth herein. In yet another embodiment, the prosthetic socket i-s can be any conventional prosthetic socket as known in the related art.

The prosthetic socket 150 has a first end 108, a second end 106, and the first end 108 has an opening 180 configured and dimensioned to receive at least a portion of a residual limb 190 of a user and the flexible inner socket 100. The second end 106 is closed end 170. A cavity or partial channel is formed extending from the open first end 108 to the closed second end 106. The cavity or channel is configured to enclose at least a portion of the residual limb 190. The volume of the cavity is greater than the volume of the residual limb.

In one embodiment, a user can position the flexible inner socket 100 on at least a portion of the residual limb 190. Next, the user can position at least a portion of their residual limb into the prosthetic socket 150 by inserting the limb through the opening 180 of the first end. Moreover, the user can position their limb with the flexible inner socket 100 to the second end 106 until the base of the residual limb 190 rests on an inner surface of the enclosed end 106.

Referring to FIG. 1C, the residual limb 190 is shown arranged in the prosthetic socket 150. For example, a lower calf portion of a residual limb is inside the prosthetic socket 150 and inside the flexible inner socket 100. The prosthetic socket 150 attaches to a prosthetic mechanical lower leg to allow a person with a below or above the knee amputation to walk using the socket plus prosthesis (not shown).

The prosthetic socket 150 includes a cup portion 160 and a base portion 170. The cup 160 is configured in a shape of a hollow deep or elongated cup that is generally substantially cylindrical in shape and has an outer surface and an inner surface. The inner surface of the cup 160 is the inner surface of the prosthetic socket 150. The circumference of the inner surface is the inner circumference of the rigid prosthetic socket 150. The cup 160 is formed with an opening 180 via which the residual limb 190 can be inserted into the cup 160.

In this embodiment, the cup 160 is shapeable after being heated at a shaping temperature. The shaping temperature can be in the range of about 150° F. to about 302° F. and any sub-range within. The shaping time can be in the range of about five minutes to about fifteen minutes, or any sub-range within. In one embodiment, the cup 160 has a pliability above a threshold pliability for a shaping time after being heated at the shaping temperature. The shaping time can be in the range of five minutes to fifteen minutes, or any sub-range within. During the shaping time, the cup 160 can be stretched circumferentially over the residual limb or a plaster model of the residual limb so that the cup 160 is shaped to fit the residual limb. No global reduction is applied to the cup 160 during the shaping. In one embodiment, the cup or prosthesis and its shaping is described with reference to U.S. patent Ser. Nos. 15/914,480 and 16/516,199 each of which is incorporated by reference as if fully set forth herein.

The base 170 joins the cup 160 to the prosthesis or is integral with the base unit. In one embodiment, the prosthesis can be a conventional prosthesis as known in the art or the prosthesis described in U.S. patent Ser. Nos. 15/914, 480 and 16/516,199 each of which is incorporated by reference as if fully set forth herein. The base can have a pliability that is lower than the pliability of the cup 160 at the shaping temperature and/or at room temperature. Optionally and/or alternatively, the base 170 and the cup 160 are constructed from the same material. The base 170 is not heated or is heated at a lower temperature than the shaping temperature when the cup 160 is heated. Optionally and/or alternatively, the base 170 is made from a different material than the cup 160.

The prosthetic socket 150 is configured to have an inner dimension to fit at least a portion of the residual limb 190. For example, the prosthetic socket 150 may have been formed directly over the residual limb 190 or over a model of the residual limb 190 without global reduction being applied. The inner surface of the rigid prosthetic socket 150 can have a contour and dimension that match, e.g., the same as or substantially similar to, the anatomical shape and dimension of the residual limb 190.

In one embodiment, after the prosthetic socket 150 has been formed, it can used to fabricate the flexible inner socket 100. For example, a preformed socket having a generic shape can be heated and molded onto the inner surface of the rigid prosthetic socket 150 to form the flexible inner socket 100. The heating temperature can be in a range from about 190° F. to about 285° F. The flexible inner socket 100 is formed on the inner surface of the prosthetic socket 150. The flexible inner socket 100, after heated and formed, therefore can have a shape matching the contour of the inner surface of the rigid prosthetic socket 150 and the anatomical shape of the residual limb 190.

In one embodiment, the flexible inner socket 100 can be attached or releasably configured on an inner surface of the prosthetic socket 150 to provide an overall inner circumference reduction of the prosthetic socket 150 based on the thickness 130 of the flexible inner socket 100. With the inner circumference reduction, the tissue of the residual limb 190 is compressed generally across the surface of the limb, and thereby bears the weight of the user. As the tissue has a larger surface area than the bone end and prominences of the residual limb 190 that might otherwise bear the weight against the hard surface of a rigid prosthetic socket, the inner circumference reduction via the compressible material of the flexible inner socket spreads the weight and causes a more comfortable fit of the prosthetic socket 150. Moreover, as described herein, the reduction reduces the inner circumference of the prosthetic socket in a predetermined manner based on the thickness of the pre-socket to provide a globally reduced fit of the prosthetic socket.

In one embodiment, the flexible inner socket 100 is fabricated on the inner surface the prosthetic socket 150, the inner circumference reduction can be precisely controlled. In some embodiments, the inner circumference reduction is controlled by controlling the thickness 130 of the flexible inner socket 100 (or the thickness of the preformed socket that is used to form the flexible inner socket 100). The thickness 130 of the flexible inner socket 100 can range from about 0.5 millimeters (mm) to about 8 mm or greater, or any sub-range within. The thickness 130 can be determined to provide an inner circumference reduction for tightening the fit on the residual limb ranging from about 3% to about 8% or sub-ranges within.

In some embodiments, the thickness 130 is the same for different portions of the flexible inner socket 100 so that the flexible inner socket 100 can provide a uniform inner circumference reduction. In other embodiments, the thickness 130 is different at different locations of the flexible inner socket 100, and the inner circumference reduction for different portions of the rigid prosthetic socket is thereby different, e.g., the thickness can be a variable thickness or any combination of thickness. The thickness 130 can be determined based on characteristics of the prosthetic socket 150 (e.g., dimensions, shapes, etc.), characteristics of the residual limb 190, characteristics of the user (e.g., weight, BMI, shape and/or dimensions of the residual limb of the patient, water retention, medical conditions, etc.), combinations of any of the same and the like. Additional features and embodiments surrounding the thickness 130 of the flexible inner socket 100 are described herein, and with reference to FIGS. 4 and 5.

In one embodiment, after the flexible inner socket 100 is formed, the opening 110 of the flexible inner socket 100 is trimmed to match the contour of the opening 180 or substantially match the contour of the opening 180 of the prosthetic socket 150. The opening 110 and the material of the flexible inner socket 100 can also be configured to extend above the opening 180 in a similar contour of the opening 180 of the prosthetic socket 150 as shown in FIG. 1B. Optionally and/or alternatively, the material of the flexible inner socket 100 extending above the prosthetic socket 150 can be folded over the opening 180 of the rigid prosthetic socket 150.

In one embodiment, the flexible inner socket 100 is less rigid than the prosthetic socket 150 so that it can provide a softer edge to the prosthetic socket 150 for absorption of one or more of impact, force, stress and to provide comfort to the user. For example, the flexible inner socket 100 can have a rigidity expressed with an A-type durometer value in a range from about 55 to about 95.

Figure 2C:
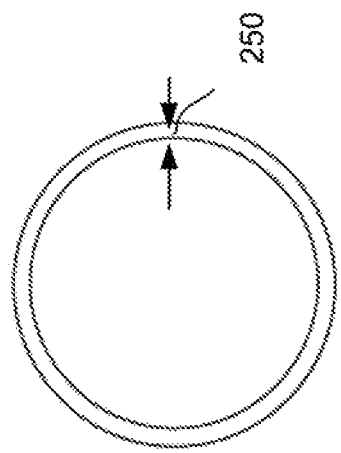
FIG. 2C is a top view of the preformed socket or pre-socket, in accordance with another embodiment.
Figure 2D:
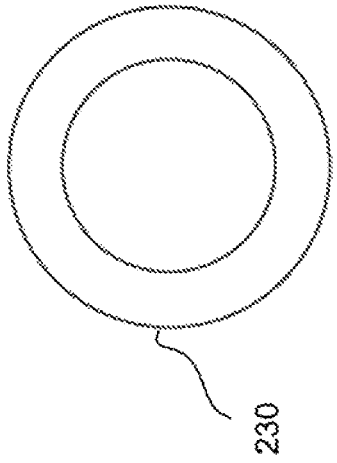
FIG. 2D is a bottom view of the preformed socket or pre-socket, in accordance with another embodiment.
Figure 2B:
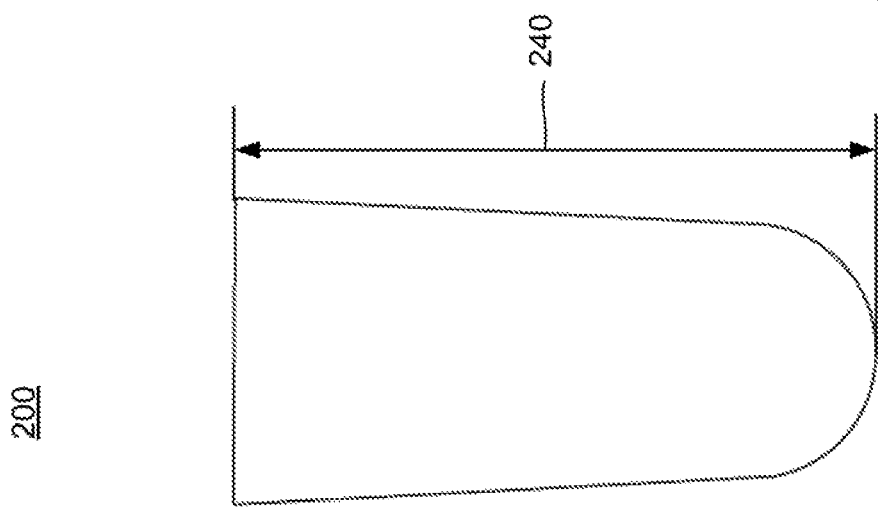
FIG. 2B is a cross-sectional view of the preformed socket or pre-socket, in accordance with another embodiment.
Figure 2A:
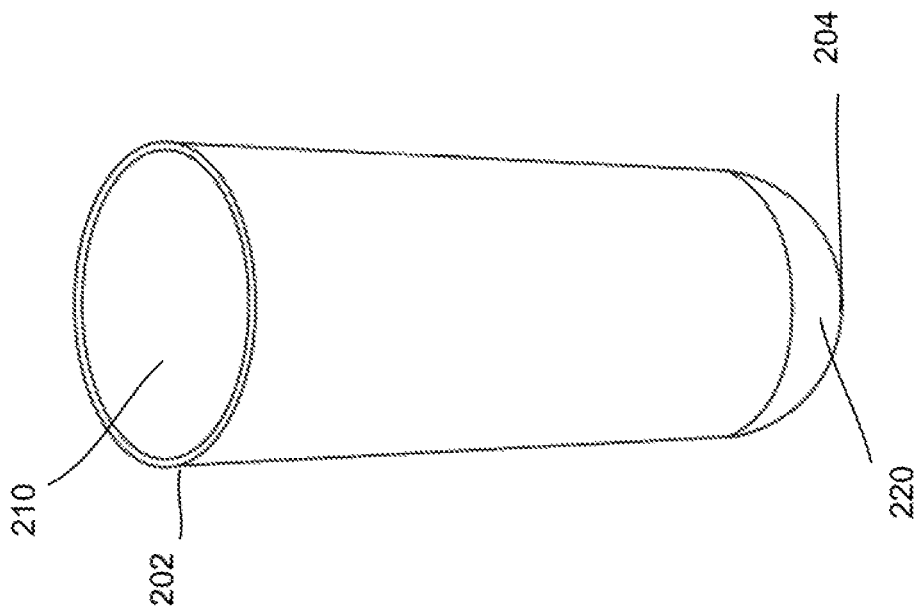
FIG. 2A is a perspective view of a preformed socket or pre-socket, in accordance with another embodiment.

FIG. 2A is a perspective view of a preformed socket or inner socket, in accordance with another embodiment. FIG. 2B is a cross-sectional view of the preformed socket, in accordance with another embodiment. FIG. 2C is a top view of the preformed socket, in accordance with another embodiment. FIG. 2D is a bottom view of the preformed socket, in accordance with another embodiment.

Referring to FIGS. 2A-2D, a perspective view of a preformed socket 200, which can be used to form a flexible inner socket, such as the flexible inner socket 100, by being molded onto the inner surface of a prosthetic socket 150. The preformed socket 200 can be formed by using a thermoformable material described herein. The thermoformable material can have one or more of the following physical properties: an A-type durometer in a range from about 55 to about 95, an elongation in a range from about 200% to about 600%, and a forming point temperature in a range from about of below about 170 F to about 300 F. Some suitable examples of a thermoformable material include one or more of a thermoplastic elastomer material, a thermoplastic polyurethane (TPU) material, a thermoplastic polyurethane foam material, a thermoplastic vulcanizate (TPV) material, a rubber material, an ultra-low density polyethylene (ULDPE) material, an ethylene vinyl acetate (EVA) material, a styrene material and blends of the same.

In one embodiment, the preformed socket 200 can be formed by using various techniques, such as injection molding, blow molding, rotational molding, 3D printing techniques (e.g., fused deposition modeling, selective laser sintering, and stereolithography), combinations of the same and the like. In some embodiments, the preformed socket 200 can include one or more layers, and each layer can be made from the same or different thermoformable material or thermoformable materials or entirely different materials, e.g., other types of thermoplastics.

The preformed socket 200 has a first end 202, a second end 204, and the first end 202 has an opening 210 configured and dimensioned to receive at least a portion of a residual limb 190 of a user. The second end 204 is closed end 220 in a rounded type orientation. Optionally and/or alternatively, the second end has a hole or channel that extends through the thickness of the preformed socket 200. A cavity or partial channel is formed extending from the open first end 202 to the closed second end 204. The enclosed end 220 is opposite to the opening 210. The enclosed end 220 can have any type geometry, e.g., square, rectangle, cone, etc. The preformed socket has an outer circumference 230, which is smaller than the inner circumference of the rigid prosthetic socket 150. A difference between the outer circumference 230 of the preformed socket 200 and the inner circumference (not shown) of the rigid prosthetic socket 150 (not shown) may be no more than 15%. In one embodiment, the circumference 230 of the preformed socket 200 can be determined based on the inner circumference of the rigid prosthetic socket 150 based on formula (1) herein or other techniques herein.

The preformed socket 200 has a length 240 that is equal to or larger than the corresponding length of the prosthetic socket 150, e.g., having a longer length than the prosthetic socket, thereby allowing the flexible inner socket 100 to be trimmed to a predetermined shape and geometry. In this embodiment, the preformed socket 200 has a thickness 250 in a range from about 2 mm to about 8 mm. The thickness 250 of the preformed socket 200 can be determined based on the desired inner circumference reduction of the prosthetic socket 150.

Optionally and/or alternatively, a kit including multiple preformed sockets 200 having different dimensions and shapes can provided to an end user to allow the end user to form multiple flexible inner sockets 100 that can provide different inner circumference reductions to the rigid prosthetic socket 100. The kit further can include instructions for use, e.g., selection and application of the different flexible inner sockets.

Figure 3:
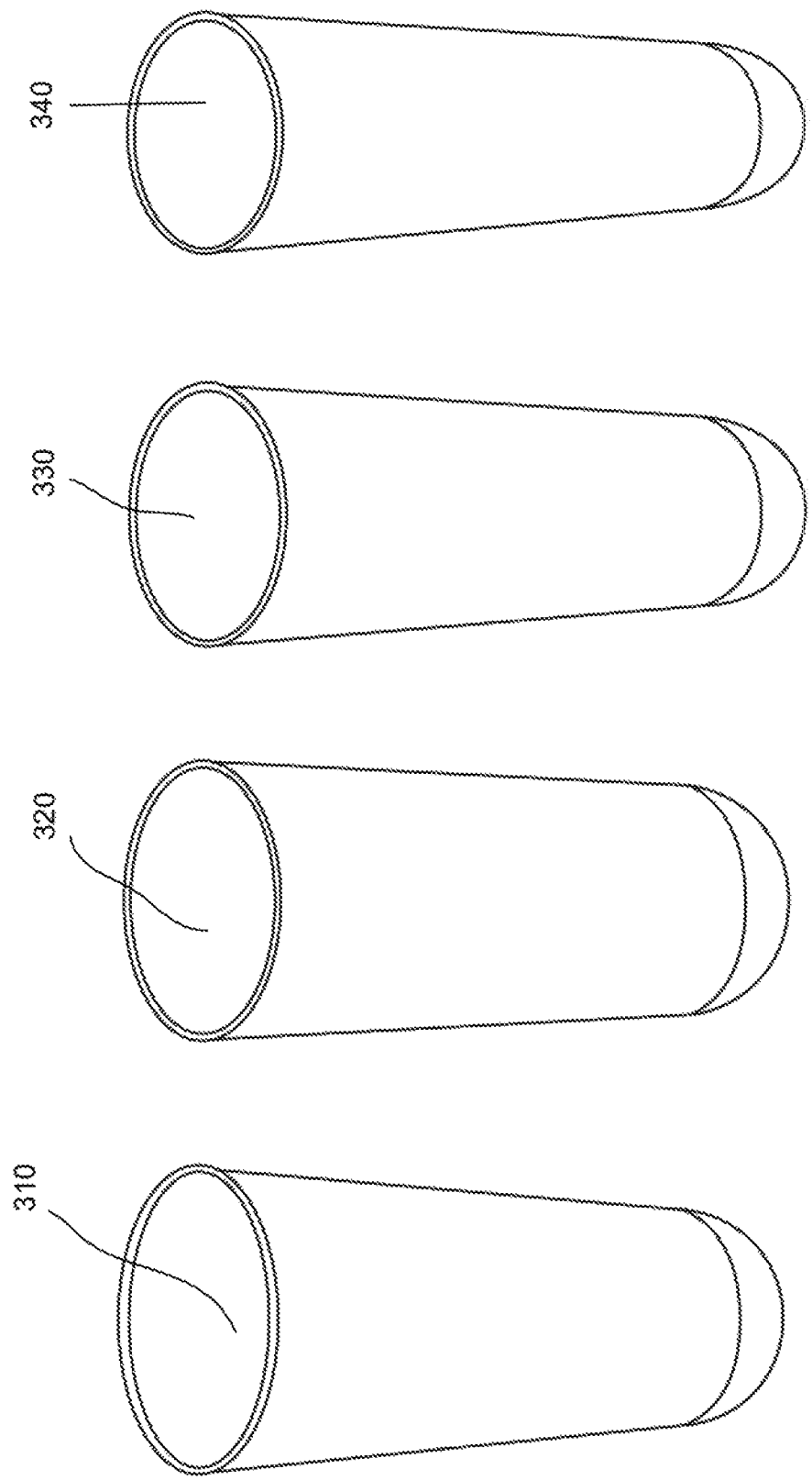
FIG. 3 illustrates a group of preformed sockets or pre-sockets having different shapes and dimensions, in accordance with another embodiment.

FIG. 3 illustrates a group of preformed sockets having different shapes and dimensions, in accordance with another embodiment.

Referring to FIG. 3, a group of preformed sockets is generally depicted with reference to preformed socket 310, preformed socket 320, preformed socket 330, and preformed socket 340. Each of these preformed sockets 310, 320, 330 and 340 have different shapes and dimensions.

Each of the preformed sockets 310, 320, 330, and 340 are different embodiments of the preformed socket 200 described with reference to FIGS. 2A-2D. Each of the preformed sockets 310, 320, 330, and 340 can be used to form a flexible inner socket (e.g., the flexible inner socket 100) that can be attached to the inner surface of a rigid prosthetic socket (e.g., the rigid prosthetic socket 150) to provide an inner circumference reduction to the prosthetic socket. Optionally and/or alternatively, the group of preformed sockets can include any number of preformed sockets.

The group of four preformed sockets 310, 320, 330, and 340 can include a different number of preformed sockets with different dimensions, thickness, materials, lengths, and other attributes described herein. In this embodiment, preformed sockets 310, 320, 330, and 340 have decreasing circumferences. Preformed socket 310 has the largest circumference and preformed socket 340 has the smallest circumference. Other dimensions, such as length, of the preformed sockets 310, 320, 330, and 340 can also be different. The preformed sockets 310, 320, 330, and 340 can also have different shapes, such as more or less conical shapes. The preformed sockets 310, 320, 330, and 340 can have ends that are rounded or oblong. They can also have uniform thickness or have different thicknesses at different portions. Optionally and/or alternatively, the second end has a hole or channel that extends through the thickness of the preformed socket.

The preformed sockets 310, 320, 330, and 340 are used for forming flexible inner sockets of different sizes. These flexible inner sockets can provide different inner circumference reductions to the same rigid prosthetic socket or multiple rigid prosthetic sockets of different sizes. In some embodiments, a user may need a flexible inner socket of a different size as conditions of the user's residual limb change. For instance, the user's residual limb can undergo substantial changes in shape and volume during the postoperative recovery period, during the day or other times. As the shape or volume of the user's residual limb changes, the user needs a different amount of inner circumference reduction for comfortable fit of the prosthetic socket. The circumference of each of the preformed sockets 310, 320, 330, and 340 is smaller than the inner circumference of the rigid prosthetic socket so that it can be placed into the prosthetics socket for being molding onto the inner surface of the prosthetic socket. In some embodiments, the difference between the circumference of each of the preformed sockets 310, 320, 330, and 340 and the inner circumference of the rigid prosthetic socket is no more than 15% so that the preformed sockets 310, 320, 330, and 340, after heated and stretched, can match the inner surface of the rigid prosthetic socket.

Figure 4:
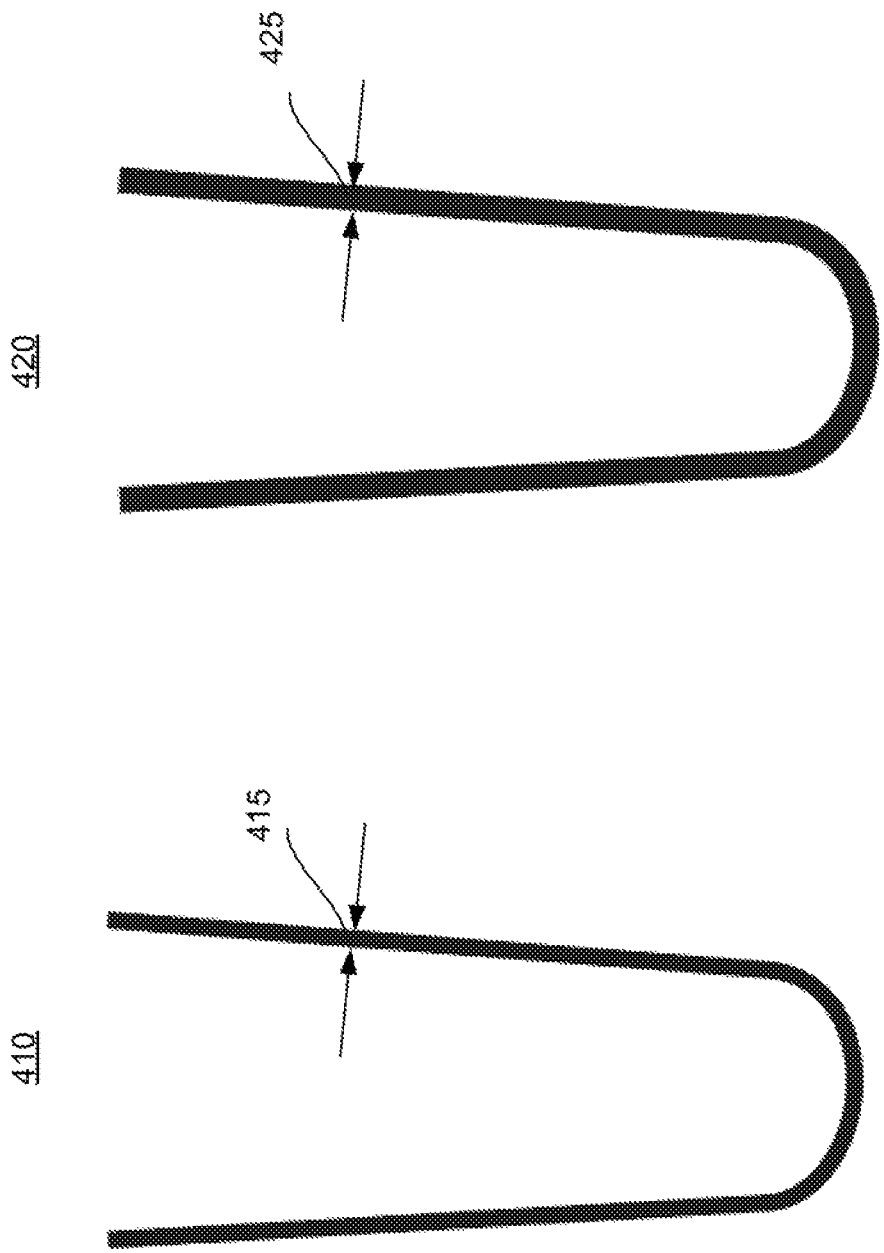
FIG. 4 illustrates cross-sectional view of two preformed sockets or pre-sockets, each of which has a uniform thickness, in accordance with another embodiment.

FIG. 4 illustrates a cross-sectional view of two preformed sockets, each of which has a uniform thickness, in accordance with another embodiment.

Referring to FIG. 4, two preformed sockets are generally depicted as 410 and 420. Each of the preformed sockets 410 and 420 have a uniform thickness. Preformed socket 410 has a thickness 415 and preformed socket 420 has a thickness 425. Thickness 425 is larger than thickness 415. The thicknesses 415 and 425 can be in a range from about 2 mm to about 8 mm.

In one embodiment, two or more preformed sockets, e.g., 410 and 420, can be used to form two flexible inner sockets of different thicknesses by molding the preformed sockets 410 and 420 onto the inner surface of a same prosthetic socket. The thickness of the flexible inner sockets can be the same or similar to the thicknesses 415 and 425 and the preformed sockets 410 and 420. The material of socket 410 and 420 can be the same or different.

In one embodiment, the two flexible inner sockets 410 and 420 can be interchangeable and removable by a user from a prosthetic. As the flexible inner sockets have different thicknesses 415 and 425, they can provide different amounts of inner circumference reduction to the same rigid prosthetic socket for a user. For example, a user can wear the flexible inner socket formed from the preformed socket 410 when the user's residual limb is engorged and larger (e.g., typically in the morning a residual limb can have a larger outer circumference), and use the flexible inner socket formed from the preformed socket 420 when the user's residual limb is shrunk and fluid has been pressed out from the residual limb (e.g., typically in the afternoon a residual limb of user can have a smaller circumference as compared to the morning).

As the preformed sockets 410 and 420 have uniform thicknesses 415 and 425, the flexible inner sockets provide uniform inner circumference reductions. The thickness of a preformed sockets can have a non-uniform distribution to form a flexible inner socket providing a non-uniform inner circumference reduction. Optionally and/or alternatively, the second end has a hole or channel that extends through the thickness of the preformed socket.

Figure 5:
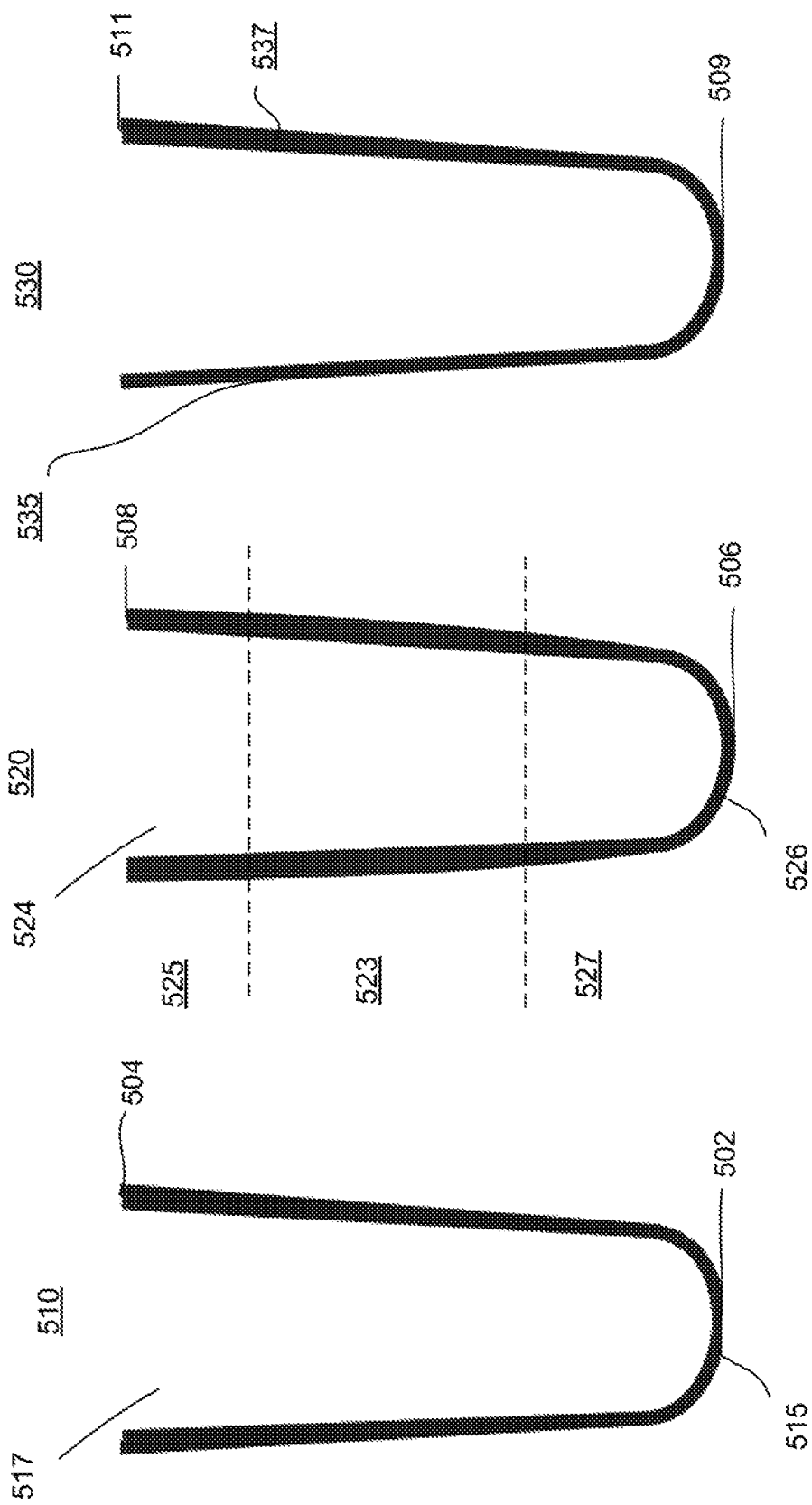
FIG. 5 illustrates pre-sockets having non-uniform thicknesses, in accordance with another embodiment.

FIG. 5 illustrates pre-sockets having non-uniform thicknesses, in accordance with another embodiment.

Referring to FIG. 5, preformed sockets 510, 520, and 530 are generally depicted each having non-uniform thicknesses as depicted in each preformed socket. Each of the preformed sockets 510, 520, and 530 can be an embodiment of the preformed socket 200 herein or any embodiment herein. Each of the preformed sockets 510, 520, and 530 has a different thickness at different portions of the preformed socket.

Preformed socket 510 has a first end 502 and second end 504. The first end 502 is enclosed 515 and the second end 504 is open 517. The thickness of the preformed socket 510 gradually increases from the first end 502 to the second end 504.

Preformed socket 520 has a first end 506 and second end 508. The first end 506 is enclosed 526 and the second end 508 is open 524. Preformed socket 520 has a first end region 527, a middle region 523 and a second end region 525. The first end region 527 has thickness less than the thickness in middle region 523. The middle region 523 has a thickness less than the thickness in the first end region 527. The thickness in first end region 527, the middle region 523 and the second end region 525 can be in a range from about 1 mm to about 8 mm or greater.

Preformed socket 530 has a first end 509, a second end 537, a left side portion 535 and right side portion 537. The left portion 535 of the preformed socket 530 has a smaller thickness than the right portion 537 of the preformed socket 530. The left side portion 535 can have a thickness in a range from about 2 mm to about 8 mm or greater and the right side portion 537 can have a thickness in a range from about 2 mm to about 8 mm or greater. Optionally and/or alternatively, there can be greater thickness at specified locations, such as where the bone prominences, etc. tend to contact the flexible inner socket. In addition, the thickness from a first end 509 to a second end 511 does not have to be linear in its rate of change from the first end 509 to the second end 511, e.g., the thickness can have any rate of change from a first end 509 to a second end 511, e.g., non-linear, linear or constant rate of change.

The thickness can be customized and optimized for a particular user's shape of their residual limb and features of the same, e.g., bone prominences, soft spots, infection, bruising, and the like. This customized and optimized thickness can be determined with computer scanner devices, manually with plaster molds, visually mapping, and any combination of the same or the like. This customized and optimized thickness can also be adjusted in-situ with tools configured to remove thickness, e.g., grinder, sander and the like.

As the preformed sockets 510, 520, and 530 have non-uniform thicknesses, they can form flexible inner sockets of non-uniform thicknesses. These flexible inner sockets, when attached to the inner surface of a rigid prosthetic socket, can provide non-uniform inner circumference reductions and cause non-uniform compression of the residual limb of a user wearing the flexible inner socket and rigid prosthetic socket. With a larger thickness of a portion of the preformed socket, the corresponding portion of the flexible inner socket can provide a higher inner circumference reduction and the corresponding portion of the user's residual limb can be more compressed.

In some embodiments, the non-uniform distribution of the thickness of a primary socket is determined based on the conditions of the user's residual limb, such as shape, dimension, as described herein. For instance, a portion of the user's residual limb may have more tissue or be stronger than other portions. This portion of the residual limb can therefore bear more weight of the user. The rigid prosthetic socket can have a more comfortable fit if more compression is applied to this portion of the residual limb. Accordingly, the corresponding portion of the preformed socket can be made thicker. The non-uniform distribution of the thickness of a primary socket can also be determined based on characteristics of the user, such as weight, BMI (body mass index), water retention, medical conditions, and the like.

In one embodiment, to form a flexible inner socket from a preformed socket, the preformed socket is heated to a temperature so that the preformed socket becomes a formable preformed socket. The formable preformed socket is placed in the prosthetic and molded onto the inner surface of the prosthetic socket such that the outer circumference of the formable pre-socket substantially follows the contours of the inner surface of the prosthetic socket, thereby reducing the inner circumference of the prosthetic socket in a predetermined manner based on the thickness of the pre-socket to provide a globally reduced fit of the prosthetic socket. As described herein, the molding of the preformed socket can be done through inserting pressure, force, e.g., air, vacuum pressure or other external pressure can be used to apply the pressure.

FIG. 6 illustrates an air inlet assembly used for molding a preformed socket, in accordance with another embodiment.

Referring to FIG. 6, an air inlet assembly 600 is used for molding a preformed socket 650. The preformed socket 650 is the preformed socket as described herein, e.g., in FIGS. 2A-2D. The preformed socket 650 has a closed first end and open second end. The second end has an opening 660. The air inlet assembly 600 can be arranged over the opening 660 and seal the second end.

The air inlet assembly 600 includes a lid 610, a hose 620, and a clamp 630. In other embodiments, the air inlet assembly 600 can include different components that have similar functions. The preformed socket 650 can also be made with an enclosed top that has a small opening for the hose 650 to insert into. The lid 610 seals the opening 660 of the preformed socket 650. The lid 610 includes a lid cover 613, a valve 615, and a socket connector 617. The lid cover 613 is configured to be placed on the opening 660 of the preformed socket 650.

The lid 610 has a top portion or cover 613 formed with a hole at a central area of the lid cover 613. The hole can include a valve 615, e.g., one-way valve, for controlling air flow. The valve 615 has a shape of a hollow cylinder. The valve 615 and the hole in the lid cover 613 provide an air channel to the preformed socket 650. The socket connector 617 is coupled to the lid cover 613 and can be inserted into the preformed socket 650 to make the preformed socket 650 airtight. The socket connector 617 can be in a shape of a ring and can be made of rubber or other flexible materials. The socket connector 617 can have a top portion that is coupled to the lid cover 613 and a bottom portion that has a larger diameter than the top portion.

In one embodiment, the hose 620 is coupled to the valve 615 of the lid 610. One end of the hose 620 is inserted into the valve 615. Another end of the hose 620 can be connected to a pump that pumps air into the preformed socket 650 through the hose 620.

The clamp 630 clamps the portion of the preformed socket 650 that encloses the socket connector 617 of the lid 610 to hold the lid 610 to the preformed socket 650, particularly the socket connector 617 of the lid 610, with the preformed socket 650.

FIGS. 7A-7D illustrate a process of molding a preformed socket onto an inner surface of a rigid prosthetic socket by using the air inlet assembly, in accordance with another embodiment;

Referring to FIGS. 7A-7D, a preformed socket 650 is molded or arranged onto an inner surface of a prosthetic socket 700 by using the air inlet assembly 600 of FIG. 6. The air inlet assembly 600 is installed on the preformed socket 650 and seals the opening 660 of the preformed socket 650.

Figure 7A:
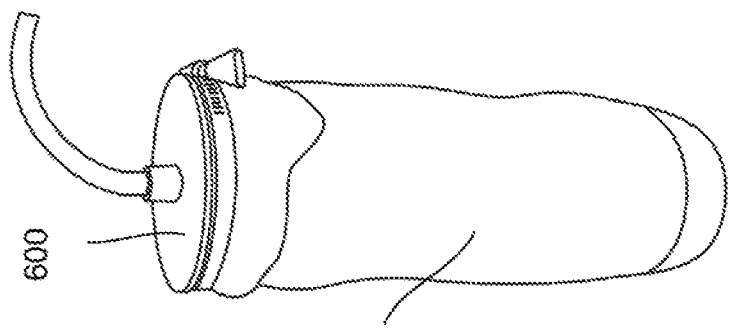
FIGS. 7A-7D illustrate a process of molding a preformed socket or pre-socket onto an inner surface of a rigid prosthetic socket by using the air inlet assembly, in accordance with another embodiment.
Figure 7B:
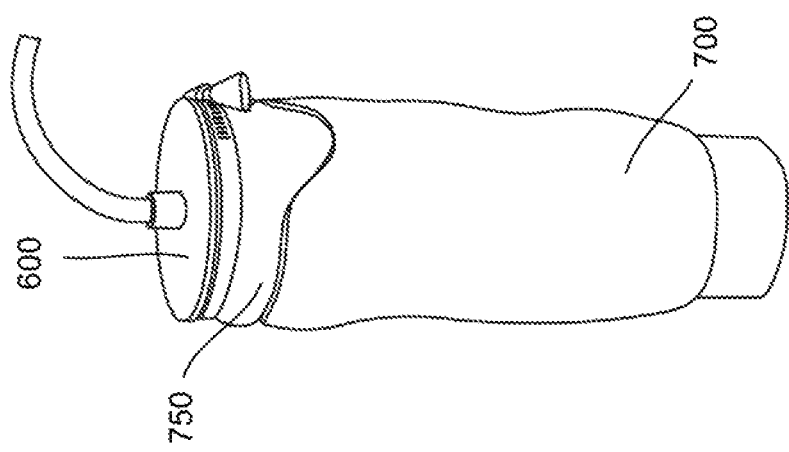

Referring to FIG. 7B, in this step, the preformed socket 650 is heated to a temperature in a range from about 200° F. to about 280° F. The preformed socket 650 becomes pliable due to the heating. The heated preformed socket 650 is placed into the rigid prosthetic socket 700.

Figure 7C:
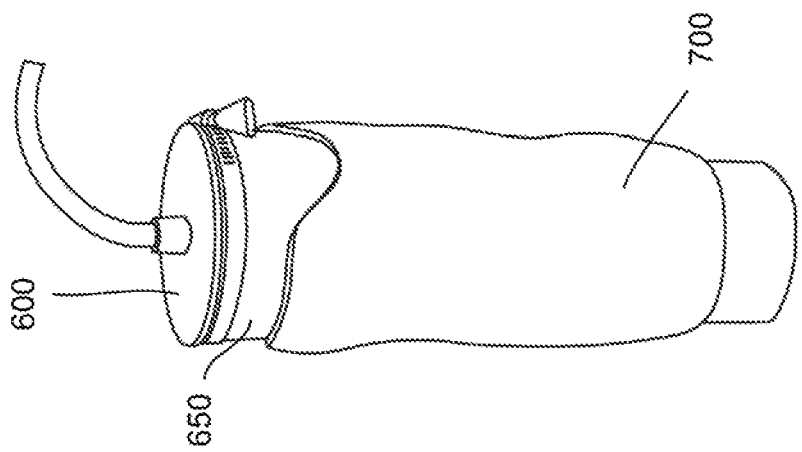

Referring to FIG. 7C, in this step, air is inserted into the preformed socket 650 by using a pump, e.g., a hand ball pump, electric pump or the like to a molding pressure. The molding pressure may be any pressure from about 1 psi to about 8 psi or greater. The pressure inflates the preformed socket 650 and presses the preformed socket 650 against the inner surface of the prosthetic socket 700. The air utilized may be heated air, cooled air or a combination throughout process.

Figure 7D:
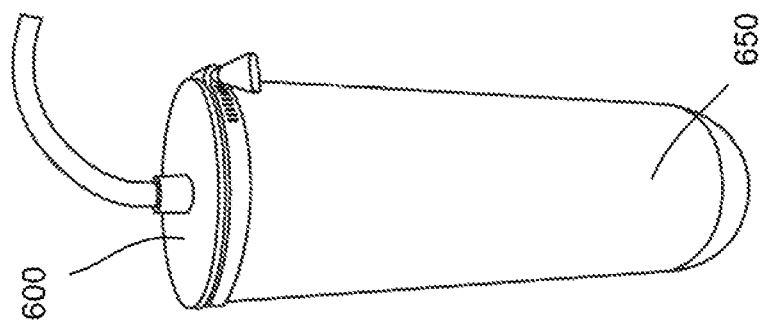

The preformed socket 650 is molded onto the inner surface of the rigid prosthetic socket 700 by the internal pressure of the preformed socket, thereby substantially conformally forming the flexible inner socket 750 to the prosthetic socket. During the molding, the preformed socket 650 is stretched and shaped to fit the contour of the inner surface of the rigid prosthetic socket 700. The flexible inner socket 750 has a shape that matches or substantially matches the contours of the inner surface of the prosthetic socket 700. The thickness of the preformed socket 650 may not change or minimally changes during the molding process. The preformed socket 650 may be heated during the insertion of the air. Referring to FIG. 7D, in this step, the flexible inner socket 750 has been formed and can now be removed from the prosthetic socket 700.

In one embodiment, the preformed socket 650 may expand out of the rigid prosthetic socket 700 during the molding process. Also, the rigid prosthetic socket 700 may have a smaller length than the preformed socket 650, and a portion of the preformed socket 650 is not enclosed in the rigid prosthetic socket 700 as shown in FIG. 7B. This portion of the preformed socket 650 is not constrained by the rigid prosthetic socket 700 and may expand in an undesired manner during the inflation, which can result in the flexible inner socket 750 having an undesired shape. Wraps can be used during the molding process to prevent undesired expansion of the preformed socket 650.

Figure 8:
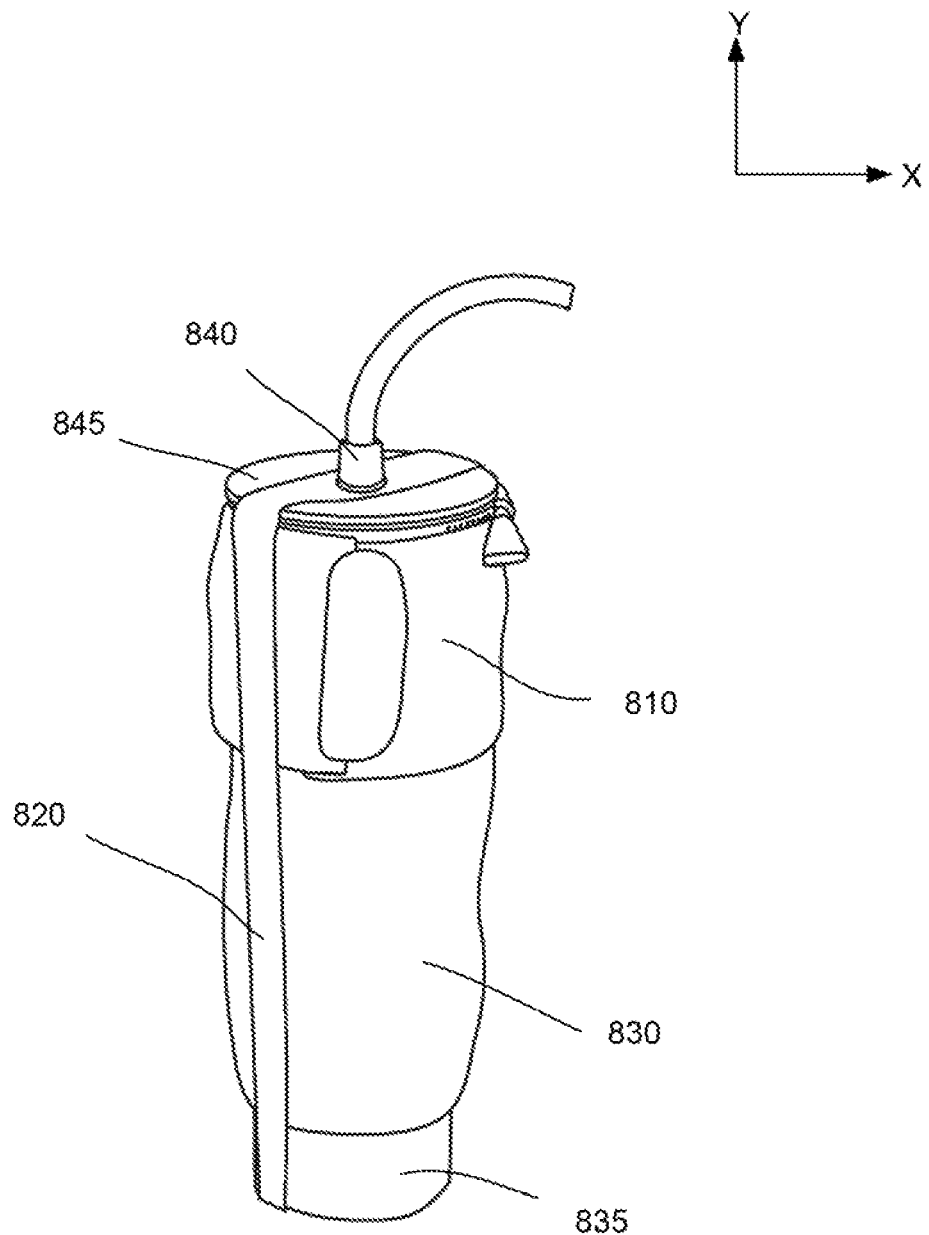
FIG. 8 illustrates wraps used for constraining a preformed socket or pre-socket during molding of the pre-socket, in accordance with another embodiment.

FIG. 8 illustrates wraps used for constraining a preformed socket during molding of the pre-socket, in accordance with another embodiment.

Referring to FIG. 8, wraps 810 and 820 are used for constraining a preformed socket during molding of the preformed socket. The preformed socket 830 can be molded onto the inner surface of a rigid prosthetic socket using the process described in conjunction with FIGS. 7A-7D.

In this embodiment, a preformed socket is placed in the prosthetic socket 830. The wraps 810 and 820 constrain the preformed socket during its inflation by the inserted air. The wraps 810 and 820 can prevent the preformed socket from expanding out of the opening of the prosthetic socket 830. Optionally and/or alternatively, one of either wrap 810 and 820 may be used. The wraps 810 and 820 can be made from Velcro bands, fabric, polymer or other materials that provide the proper amount of constraint.

The wrap 810 circumferentially wraps a portion of the prosthetic socket 830 to constrain expansion of the preformed socket. The wrap 810 can also circumferentially wraps a portion of the preformed socket, such as a portion of the preformed socket that is not enclosed in the rigid prosthetic socket 830. The wrap 810 reduces circumferential expansion of the preformed socket.

The wrap 820 wraps the prosthetic socket 830 and is arranged over the top surface of the lid 845 of the air inlet assembly 840 the sides of the rigid prosthetic socket 830, and the bottom of the base 835 of the prosthetic socket 830. The preformed socket is enclosed within the lid 845 of the air inlet assembly 840 and the prosthetic socket 830, so that the wrap 820 prevents the preformed socket from expanding vertically along a y-axis.

Figure 9:
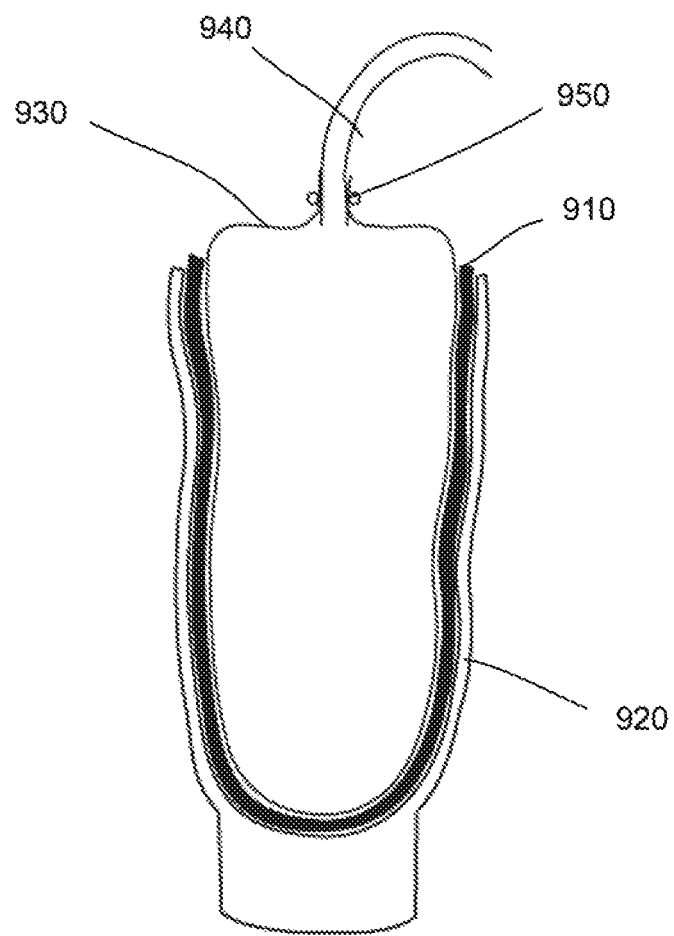
FIG. 9 illustrates a process of molding a preformed socket onto an inner surface of a rigid prosthetic socket by using an air bag, in accordance with another embodiment.

FIG. 9 illustrates a process of molding a preformed socket onto an inner surface of a rigid prosthetic socket by using an air bag, in accordance with another embodiment.

Referring to FIG. 9, a process of molding a preformed socket 910 onto an inner surface of a rigid prosthetic socket 920 by using an air bag 930 is generally described. The preformed socket 910 can be the preformed socket 200 or any preformed socket described herein. The prosthetic socket 920 can be a rigid prosthetic socket 150 or any prosthetic socket described herein.

In a first step, the preformed socket 910 is placed in the prosthetic socket 920. Next, the airbag 930 is placed in the preformed socket 910. The airbag 930 is coupled to a hose 940, through which air source or pump can be coupled to the airbag 930. The hose 940 is coupled to a valve 950 that controls flow of the air. For instance, air can be inserted into the air bag 930 when the valve 950 is open and is prevented from flowing into the air bag when the valve 950 is closed.

The preformed socket 910 is heated before and/or while the air is inserted into the air bag 940 with heated air or other heat source. Due to the heating, the preformed socket 910 is pliable and configured to move from a first orientation to a second orientation. The airbag 940 is inflated by the air and press the preformed socket 910 against the inner surface of the rigid prosthetic socket 920 to mold the material of the preformed socket 910 to a contour of the inner surface of the prosthetic socket 920. The molded shape is maintained when it cools down to room temperature. After it is cooled the pressure or air source is released.

Figure 10B:
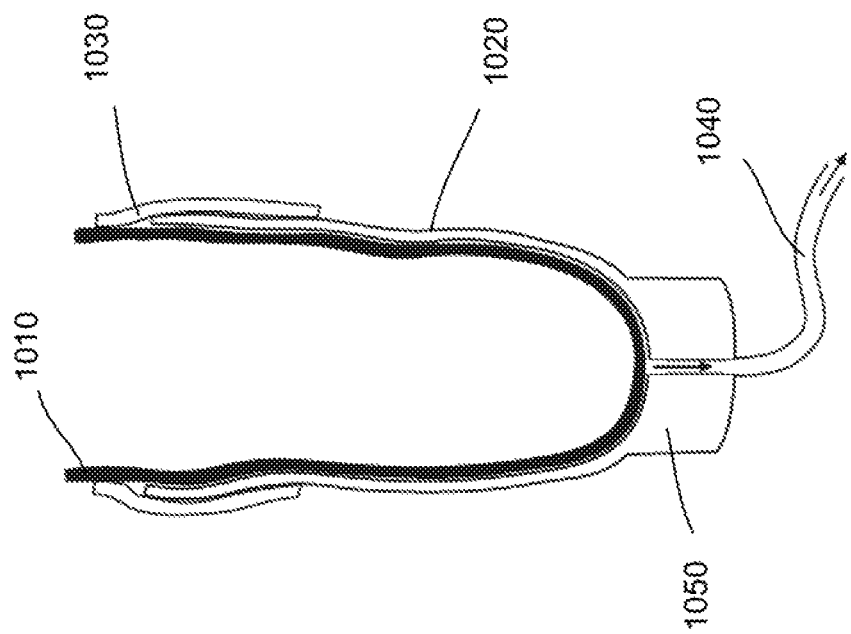
FIG. 10B is a cross-sectional view of the system, in accordance with another embodiment.
Figure 10A:
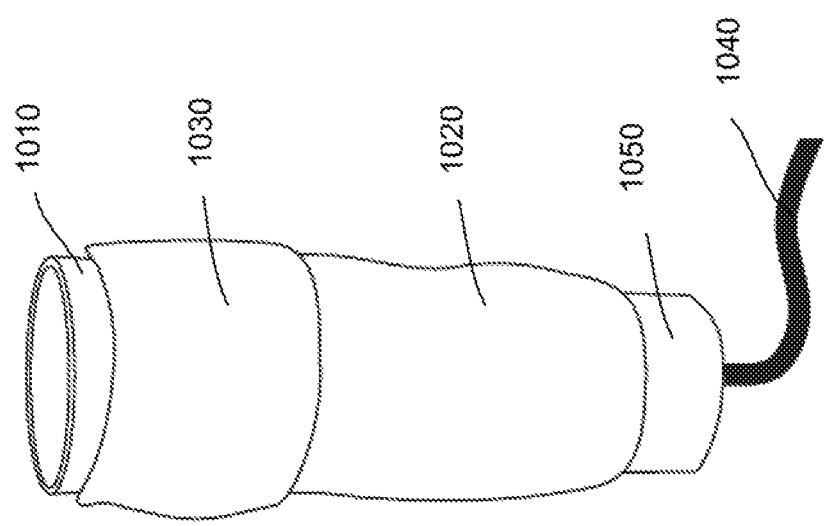
FIG. 10A is a perspective view of a system of molding a preformed socket onto an inner surface of a rigid prosthetic socket by vacuum, in accordance with another embodiment.

FIG. 10A is a perspective view of a system of molding a preformed socket onto an inner surface of a rigid prosthetic socket by vacuum, in accordance with another embodiment. FIG. 10B is a cross-sectional view of the system, in accordance with another embodiment.

Referring to FIGS. 10A-10B, a preformed socket 1010 is molded onto an inner surface of a prosthetic socket 1020 by vacuum pressure form a vacuum source with an aid of a sleeve 1030 and a vacuum hose 1040. The preformed socket 1010 is placed into the prosthetic socket 1020. A portion of the preformed socket 1010 is enclosed by the rigid prosthetic socket 1020 and another portion of the preformed socket 1010 is outside the rigid prosthetic socket 1020. For the portion of the preformed socket 1010 that is enclosed by the prosthetic socket 1020, there is a gap between the outer surface of the preformed socket 1010 and the inner surface of the prosthetic socket 1020. The gap is sealed by the sleeve 1030. As shown in FIG. 10B, the sleeve 1030 is applied on the rigid prosthetic socket 1020 and the portion of the preformed socket 1010 that is outside the rigid prosthetic socket 1020.

A vacuum hose 1040 is installed on the base 1050 of the rigid prosthetic socket 1020. The vacuum hose 1040 provides a channel to the gap between the preformed socket 1010 and the rigid prosthetic socket 1020. The vacuum hose 1040 is coupled to a vacuum source (not shown). In FIG. 10B, the air in the gap between the preformed socket 1010 and the rigid prosthetic socket 1020 is pumped out from the gap by the vacuum pump to create a vacuum, or near vacuum, in the gap. The preformed socket 1010 is pliable during creation of the vacuum by application of heat or previous application of heat that has been applied or is being applied to the preformed socket 1010. Due to the vacuum pressure, the preformed socket 1010 is pulled toward the inner surface of the rigid prosthetic socket 1020 to mold onto the inner surface of the rigid prosthetic socket 1020 and to form a flexible inner socket.

Figure 11:
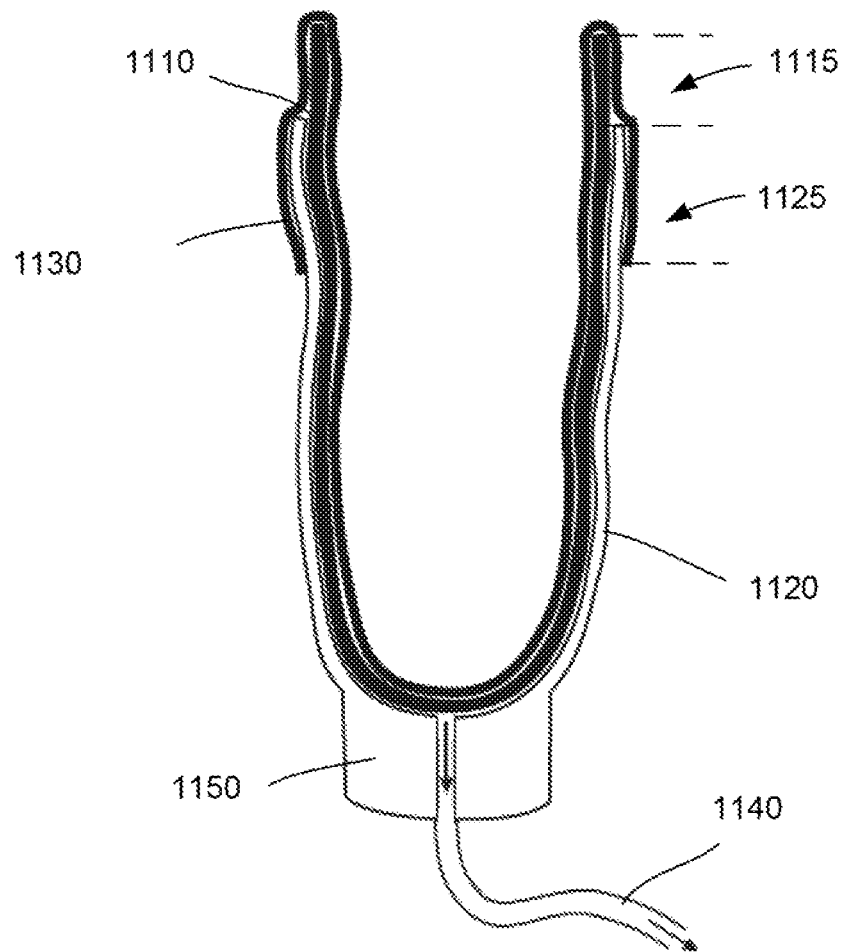
FIG. 11 illustrates another system of molding a preformed socket onto an inner surface of a rigid prosthetic socket by vacuum, in accordance with another embodiment.

FIG. 11 illustrates another system of molding a preformed socket onto an inner surface of a rigid prosthetic socket by vacuum, in accordance with another embodiment.

Referring to FIG. 11, a preformed socket 1110 is molded onto an inner surface of a prosthetic socket 1120 by vacuum. The preformed socket 1110 is placed in the prosthetic socket 1120 and a top portion 1115 of the preformed socket 1110 extends outside the opening of the prosthetic socket 1120. A flexible bladder 1130 is arranged around the preformed socket 1110 and extends outside the opening of the prosthetic socket 1120 and is folded around the top portion 1125 of the prosthetic socket 1120 to cover a portion of the prosthetic socket 1120.

In this embodiment, the flexible bladder 1130 wraps into the preformed socket 1110 and over the top portion 1115 of the preformed socket 1110 and the top portion 1125 of the rigid prosthetic socket 1120. As shown in FIG. 11, the flexible bladder 1130 covers the inner surface of the preformed socket 1110, the outer surface of the top portion 1115 of the preformed socket 1110, and the outer surface of the top portion 1125 of the prosthetic socket 1120. The flexible bladder 1130 provides a seal the gap between the preformed socket 1110 and the prosthetic socket 1120. The flexible bladder is stretched over the top portion 1115 and top portion 1125.

The vacuum hose 1140 connects to a vacuum source (not shown) and is operated to create a vacuum pressure, or near vacuum pressure, in the gap. The vacuum hose 1140 can be the same as the vacuum hose 1040. Due to the vacuum pressure, the preformed socket 1110 is molded onto the inner surface of the rigid prosthetic socket 1120 and to form a flexible inner socket. Optionally and/or alternatively, the second end of the preformed socket 1110 has a hole or channel that extends through the thickness of the preformed socket. The hole or channel (not shown) allows the vacuum pressure to communicate directly with the preformed socket through the hole or channel. In this embodiment, the preformed socket is heated prior to inserting into the prosthetic socket to a thermoformable temperature. The preformed socket is allowed to cool and the vacuum source is turned off.

Figure 12B:
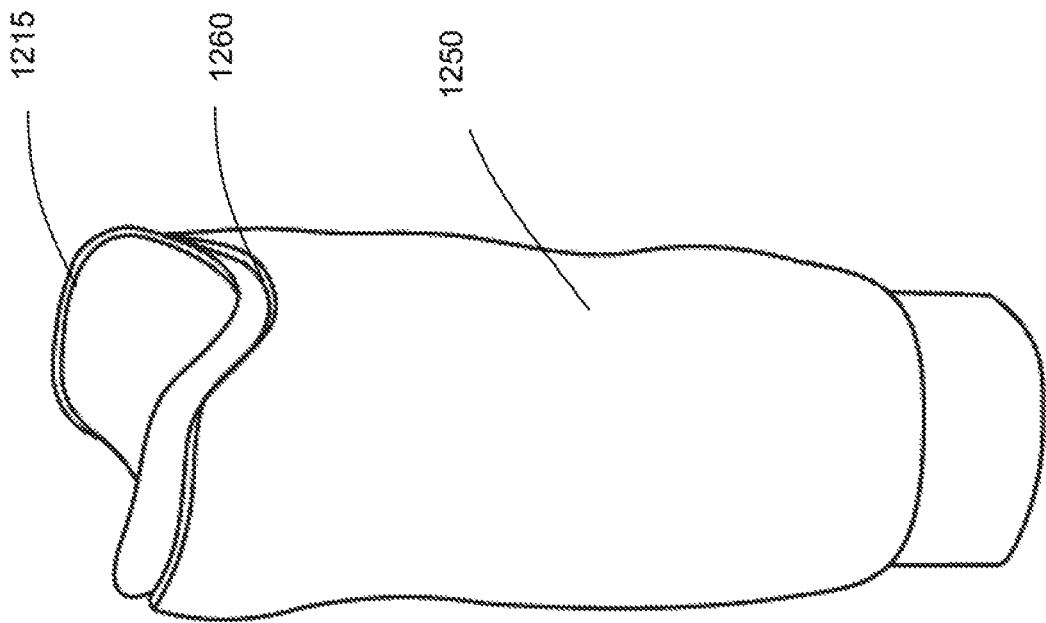
FIGS. 12A-12B illustrate a process of trimming a flexible inner socket 1200, in accordance with another embodiment.
Figure 12A:
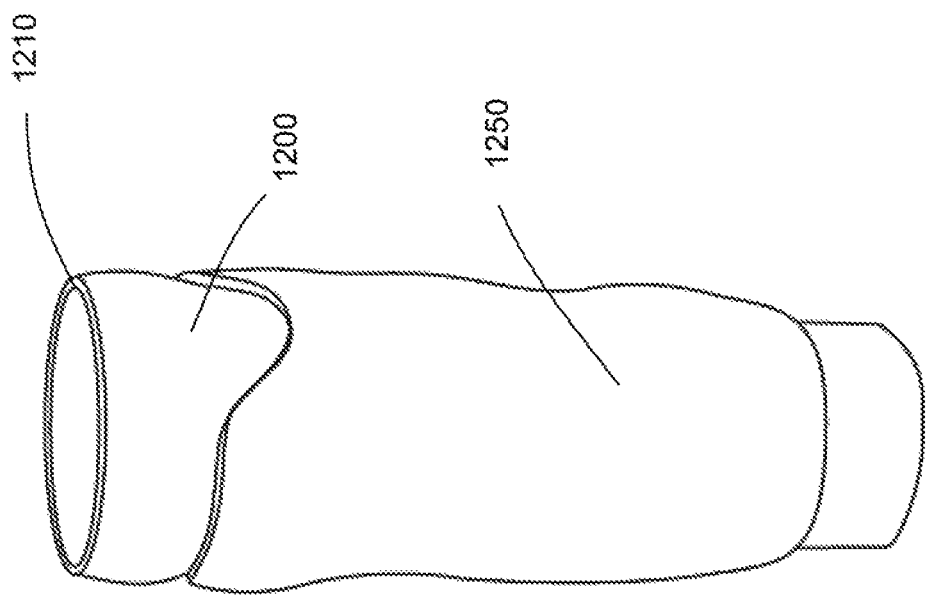

FIGS. 12A-12B illustrates a process of trimming a flexible inner socket 1200, in accordance with another embodiment.

Referring to FIG. 12A, a first flexible inner socket 1200 having a top edge 1210 untrimmed extending above a prosthetic socket 1250 is shown. In FIG. 12B, the top edge 1210 is trimmed to top edge 1215 to follow the top edge 1260 of the prosthetic socket 1250. The flexible inner socket 1200 is used to provide inner circumference reduction to a rigid prosthetic socket 1250. The flexible inner socket 1200 is formed by molding a preformed socket onto the inner surface of the rigid prosthetic socket 1250 as described in embodiments herein.

More specifically, the flexible inner socket 1200 has a top edge 1210 that forms the opening of the flexible inner socket 1200. The rigid prosthetic socket 1250 has a top edge 1260 that forms the opening of the prosthetic socket 1250. An embodiment of the flexible inner socket 1200 can be the flexible inner socket 100, and an embodiment of the rigid prosthetic socket 1250 can be the prosthetic socket 150.

Before the trimming, the flexible inner socket 1200 has a flat top edge 1210, as shown in FIG. 12A. The trimming of the flexible inner socket 1200 includes trimming the top edge 1210 to make it match the top edge 1260 of the prosthetic socket 1250. As shown in FIG. 12B, the trimmed top edge 1215 of the flexible inner socket 1200 has a contour that is the same as or similar to the contour of the top edge 1260 of the rigid prosthetic socket 1250. In some embodiments, the length of the flexible inner socket 1200 after the trimming is larger than the length of the rigid prosthetic socket 1250 so that the top edge 1215 of the flexible inner socket 1200 can be bent, e.g., while being heated by a heat gun, to cover the top edge 1260 of the rigid prosthetic socket 1250. The flexible inner socket 1200 can be softer than the rigid prosthetic socket 1250 so that it is more comfortable for the user's residual limb to contact the flexible inner socket 1200 than the prosthetic socket 1250.

Even though the flexible inner socket 1200 is placed in the prosthetic socket 1250 in FIGS. 12A-12B, the flexible inner socket 1200 can be removed from the prosthetic socket 1250 before the trimming.

Figure 13:
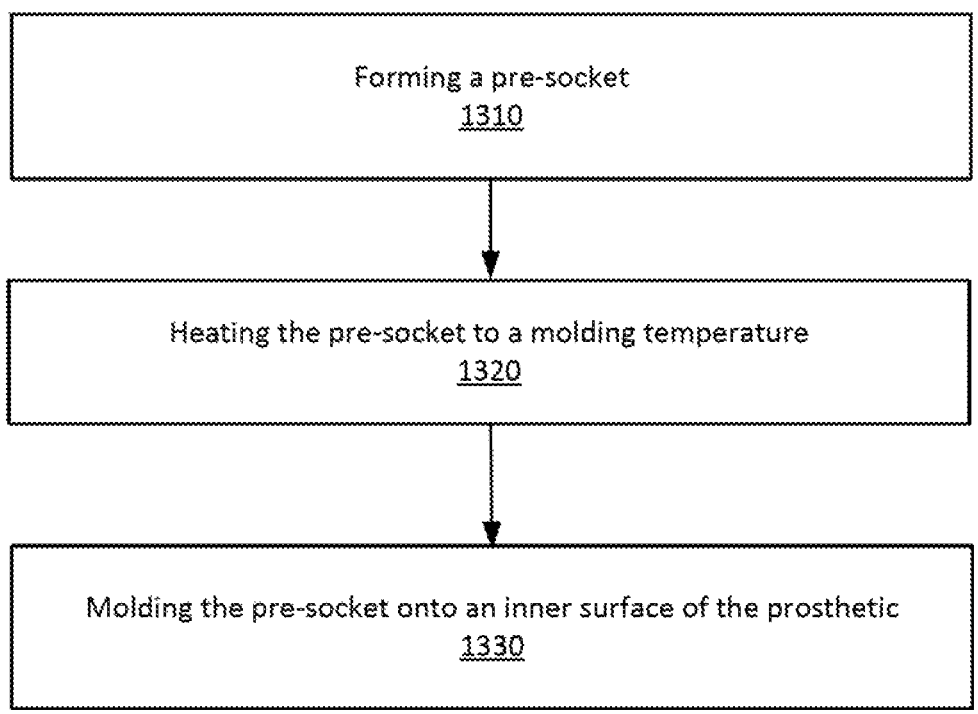
FIG. 13 illustrates a flow chart of a process for fabricating a flexible inner socket, in accordance with another embodiment.

FIG. 13 illustrates a flow chart of a process for fabricating a flexible inner socket, in accordance with another embodiment.

Referring to FIG. 13, the process of fabricating a flexible inner socket is generally shown. The flexible inner socket is used for reducing an inner circumference of a prosthetic socket, e.g., rigid, socket, that has previously been formed to fit a residual limb of a user. The process may include different or additional steps than those described in conjunction with FIG. 13 in some embodiments or perform steps in different orders than the order described in conjunction with FIG. 13.

A pre-socket is formed (step 1310) with a material. The pre-socket is formed with an opening and an enclosed end. The enclosed end is opposite the opening. A circumference of the body is smaller than the inner circumference of the prosthetic socket. For example, the circumference of the body can be up to 15% smaller than the inner circumference of the rigid prosthetic socket.

In some embodiments, the thermoformable material is a polymer material having one or properties: an A-type durometer in a range from about 55 to about 85, an elongation of at least 300%, and a melting point below about 140° C. The material can be a thermoplastic elastomer material, a thermoplastic polyurethane (TPU) material, a thermoplastic polyurethane foam material, a thermoplastic vulcanizate (TPV) material, a rubber material, an ultra-low density polyethylene (ULDPE) material, an ethylene vinyl acetate (EVA) material, a styrene material and blends of the same, combination of the same or the like. The pre-socket can be formed through one more of injection molding, rotational molding, 3D printing (e.g., fused deposition modeling, selective laser sintering, or stereolithography), blow molding, combinations of the same and the like.

In some embodiments, a thickness of the pre-socket is pre-determined, e.g., based on the dimensions of the prosthetic socket, shape and dimensions of the user's residual limb, the user's health conditions, or some combination thereof. In one embodiment, the pre-socket has a uniform thickness. In another embodiment, different portions of the pre-socket have different thicknesses as described herein.

In step 1320 the pre-socket is heated at a temperature between 90° C. to 140° C. The pre-socket becomes pliable due to the heat. After the heating 1320, the flexible inner socket is formed 1330 by molding the pre-socket onto the inner surface of the rigid prosthetic socket. The rigid prosthetic socket has been formed to fit a residual limb of a user. The rigid prosthetic socket can be formed on the residual limb of the user or on a model of the residual limb so that the inner surface of the rigid prosthetic socket has a contour and dimensions matching the anatomical shape of the residual limb. No global reduction was applied to the rigid prosthetic socket during the forming of the rigid prosthetic socket.

In some embodiments, the pre-socket is molded onto the inner surface of the rigid prosthetic socket by inserting air into the pre-socket. The pre-socket can be sealed with an air inlet assembly to form an enclosed space. The sealed pre-socket is placed in the rigid prosthetic socket. Air is inserted into the pre-socket to inflate the pre-socket. The air can press the pre-socket against the inner surface of the rigid prosthetic socket to form the flexible inner socket. In some other embodiments, the pre-socket is molded onto the inner surface of the prosthetic socket by creating vacuum pressure in a gap between the pre-socket and the rigid prosthetic socket. The vacuum pressure can pull the pre-socket toward the inner surface of the rigid prosthetic socket to form the flexible inner socket. The outer surface of the formed flexible inner socket has a contour and dimensions matching the contour and dimensions of the inner surface of the rigid prosthetic socket. The flexible inner socket can then be cooled down, e.g., to room temperature.

The flexible inner socket can be trimmed after being removed from the rigid prosthetic socket. For instance, the top edge of the flexible inner socket is trimmed to match the top edge of the rigid prosthetic socket. The flexible inner socket can be placed into the rigid prosthetic socket for use by the user.

EXAMPLES

Without intending to limit the scope of the invention, the following examples illustrate how various embodiments of the invention may be made and/or used.

Example 1

This example illustrates the manufacture of flexible inner socket according to an aspect of the invention. A pre-socket was made with a thermoformable polyurethane material GLS Versaflex CE 3115 that was durometer 65 A. It was injection molded on a 500 ton injection press. It was conical in shape and measured 30 cm tall, 11.5 cm diameter at the open proximal end, 94 cm in diameter at the substantially closed distal end, and was 2.2 mm thick uniformly from the proximal end to the distal end.

A rigid heat formable injection molded prosthetic socket was provided for a below-the-knee amputee as described with reference to U.S. patent Ser. Nos. 15/914,480 and 16/516,199, both of which are hereby incorporated by reference as if fully set forth herein. The rigid prosthetic socket was formed by heating it to 250° F. and forming it directly to the user's residual limb, that had a gel/fabric liner applied, without the typical global reduction being applied. It included first end, a second end, an inner circumference. The first end including opening and the second end was substantially closed. The forming result was that the inner socket surface had contours that substantially mimic or matched contours of a residual limb of user. The rigid prosthetic socket was trimmed to size and the edges were buffed and rounded. The pre-socket was slightly smaller externally than the rigid prosthetic socket was internally so it could be fit inside easily. The rigid prosthetic socket had a vacuum tube attached to a small opening in the distal end that was connected to an electric vacuum pump.

The pre-socket was heated with a Nutrichef infrared circulating oven model no. PKRT97 to 250° F. for 10 minutes. It was suspended on an armature to hold it shape and became pliable yet not sticky or difficult to handle with gloves. The heated pre-socket was inserted into the rigid prosthetic socket which was room temperature. A flexible closed end bladder was quickly dropped inside the pre-socket and the open end was wrapped over the top and fit tightly to the outside of the rigid prosthetic socket forming a seal. The vacuum pump was immediately turned on and the resulting vacuum immediately pulled the heated pliable pre-socket to the interior shape of the rigid prosthetic socket in every detail. The pre-socket was allowed to cool while maintaining this shape under vacuum.

A marker was used to make a trim line that extended from 1 cm to 2 cm above the edge of the rigid prosthetic socket. The formed pre-socket was removed and cut with shears to shape. The edge was ground with a buffing tool to be smooth and rounded. A small hole was made in the distal end for the purpose of using a vacuum suspension retention system to hold the socket to the limb. It was inserted back inside the rigid prosthetic socket and referred to as a flexible inner socket. A heat gun was used to heat the edges of it to flare them and accommodate the needs of the user.

The resulting product was a flexible inner socket that globally reduced the inner circumference of the rigid prosthetic socket by about 4% in a relatively precise manner. Metal fittings, a pylon, and prosthetic foot were attached. The user donned their gel/fabric inner and stepped into the device. It is critical that the global reduction compresses the flesh and muscle in a conical fashion thereby relieving pressure to the bone end and bearing the users user's weight evenly on the limb. The user walked on the prosthetic for several minutes and proclaimed that it was very comfortable and supported the weight away from the bone end adequately. A proper global reduction had been achieved.

After some more use, the user had some painful pressure on the distal anterior end as can often happen with use. The area was marked and the prosthetic was removed. The prosthetic socket, being heat formable, had the area heated with a heat gun and the flexible inner socket was removed and also heated in the same area to about 225° F. It was quickly reassembled and the user stepped in. The pressure point was relieved as the limb pressed the heat softened layers out. The pre-socket and prosthetic socket were cooled, and the result was a very comfortable good fitting prosthetic socket that the user was able to wear successfully. Both the pre-socket and the prosthetic socket are readily adjustable as described herein.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A method of forming a flexible inner socket, comprising
providing a rigid prosthetic socket configured to fit at least a portion of a residual limb of a user, wherein the rigid prosthetic socket comprises a first end, a second end, an inner circumference, the first end having an opening, the second end being substantially closed, and an inner surface having contours that substantially mimic contours of the residual limb, wherein the rigid prosthetic socket has not been globally reduced in dimension, was insufficiently globally reduced, or, as a result of residual limb volume reduction, provides insufficient global reduction;
providing a flexible pre-socket comprising a thermoformable material, wherein the flexible pre-socket comprises a first end, a second end, a thickness, an inner circumference, and an outer circumference, the first end having an opening, and the second end being substantially closed;
heating the thermoformable material of the flexible pre-socket to a temperature so that the flexible pre-socket becomes a formable flexible pre-socket;
arranging at least a portion of the formable flexible pre-socket into the rigid prosthetic socket;
molding the formable flexible pre-socket onto the inner surface of the rigid prosthetic socket such that the outer circumference of the formable flexible pre-socket substantially follows the contours of the inner surface of the rigid prosthetic socket, thereby reducing the inner circumference of the rigid prosthetic socket in a predetermined manner based on the thickness of the flexible pre-socket to provide a globally reduced fit of the rigid prosthetic socket, and thereby forming the flexible inner socket, and
wherein the molding the formable flexible pre-socket onto the inner surface of the rigid prosthetic socket further comprises using a vacuum pressure such that the outer circumference of the formable flexible pre-socket substantially follows the contours of the inner surface of the rigid prosthetic socket.

2. The method of claim 1, wherein a difference between the outer circumference of the flexible pre-socket and the inner circumference of the rigid prosthetic socket is no more than about fifteen percent (15%).

3. The method of claim 1, further comprising:
determining the thickness of the flexible pre-socket based on the inner circumference of the rigid prosthetic socket so as to achieve a desired global reduction according to Formula (1):

$$T = C/(2 \cdot \pi) \cdot X/100 \qquad \text{Formula (1)}$$

wherein T is the thickness of the flexible pre-socket [mm], C is the inner circumference of the rigid prosthetic socket that has not been globally reduced in dimension [mm], and X is a global reduction %.

4. The method of claim 1, wherein the thickness of the flexible pre-socket is a range from about 2 mm to about 8 mm.

5. The method of claim 1, wherein the thermoformable material comprises one or more of a thermoplastic elastomer material, a thermoplastic polyurethane (TPU) material, a thermoplastic polyurethane foam material, a thermoplastic vulcanizate (TPV) material, a rubber material, an ultra-low density polyethylene (ULDPE) material, an ethylene vinyl acetate (EVA) material, a styrene material and blends of the same.

6. The method of claim 1, wherein the thermoformable material comprises a material selected from the group of a closed cell foam material, a non-compressible material and a compressible material.

7. The method of claim 1, wherein the thermoformable material has one or more of the following physical properties: an A-type durometer in a range from about 55 to about 95, an elongation in a range from about 200% to about 600%, and a forming point temperature in a range from about of below about 170° F. to about 300° F.

8. The method of claim 1, wherein the heating the thermoformable material of the flexible pre-socket to a temperature so that the flexible pre-socket becomes a formable flexible pre-socket comprises heating the flexible pre-socket to a temperature in a range from about 225° F. to about 280° F.

9. The method of claim 1, wherein the molding the formable flexible pre-socket onto the inner surface of the rigid prosthetic socket further comprises:
 providing a flexible bladder;
 arranging the flexible bladder around the formable flexible pre-socket and the opening of the rigid prosthetic socket such that flexible bladder extends outside the opening of the rigid prosthetic socket and is folded around a top portion of the rigid prosthetic socket and the flexible pre-socket creating a sealed region; and
 providing a vacuum to the sealed region to mold and pull an outer surface of the formable flexible pre-socket against an inner surface of the rigid prosthetic socket.

10. The method of claim 1, wherein the flexible pre-socket comprises a thickness in a range from about 2 mm to about 8 mm.

11. The method of claim 10, wherein the flexible pre-socket comprises a thickness in a first portion that is different than a thickness in a second portion.

12. The method of claim 1, wherein the thermoformable material comprising two or more layers of material, each layer comprising a different material.

13. The method of claim 1, further comprises:
 adjusting the rigid prosthetic socket so that it has new contours on the inner surface that are different than the contours that substantially mimic contours of the residual limb;
 providing the molded flexible pre-socket;
 heating the molded flexible pre-socket to a temperature so that the molded flexible pre-socket becomes a reheated formable flexible pre-socket; and
 re-molding the formable flexible pre-socket onto the inner surface of the rigid prosthetic socket such that the outer circumference of the formable flexible pre-socket substantially follows the new contours of the inner surface of the rigid prosthetic socket.

14. The method of claim 1, wherein the flexible pre-socket is formed with a blow molding.

15. The method of claim 1, wherein the flexible pre-socket is formed with injection molding.

16. The method of claim 1, wherein the flexible pre-socket is three-dimensionally printed.

17. The method of claim 1, wherein the thermoformable material comprising a foam material.

18. The method of claim 1, wherein the first end of the flexible pre-socket extends past the open first end of the rigid prosthetic socket after it is molded.

19. The method of claim 18, further comprising removing at least a portion of the molded flexible pre-socket that extends past the first end of the rigid prosthetic socket that is open so that the first end of the molded flexible pre-socket substantially follows a geometry of the first end of the rigid prosthetic socket.

20. The method of claim 1, wherein the heating the thermoformable material of the flexible pre-socket to a temperature so that the flexible pre-socket becomes a formable flexible pre-socket comprises heating with a heat source.

21. The method of claim 20, wherein the heat source comprises an infrared heater, convection oven, silicone pad heater, halogen tube heater or other common heating devices.

22. The method of claim 1, wherein the thickness of the flexible pre-socket from the first end to the second is non-uniform.

23. The method of claim 1, wherein the thickness of the flexible pre-socket on a first side is different than the thickness on a second side.

24. The method of claim 1, wherein the molding the formable flexible pre-socket onto the inner surface of the rigid prosthetic socket further comprises:
 providing a flexible bladder;
 arranging the flexible bladder into the flexible pre-socket such the flexible bladder extends outside the flexible pre-socket and wraps around the first end of the flexible pre-socket;
 connecting a vacuum source to a channel in a base; and
 molding the formable flexible pre-socket onto the inner surface with a vacuum pressure from the vacuum source of the rigid prosthetic socket such that a portion of the flexible bladder presses against an inner circumference so that the outer circumference of the formable flexible pre-socket substantially follows the contours of the inner surface of the rigid prosthetic socket, thereby reducing the inner circumference of the rigid prosthetic socket in a predetermined manner based on the thickness of the flexible pre-socket to provide a globally reduced fit of the rigid prosthetic socket.

25. The method of claim 24, wherein the flexible bladder comprises a thermoplastic material.

26. The method of claim 24, wherein the vacuum source comprises a vacuum pump.

27. The method of claim 24, wherein the vacuum pressure comprises a vacuum pressure in a range from about 5 PSIA to about 14.7 PSIA.

28. A method of forming a flexible inner socket, comprising:
 providing a rigid prosthetic socket configured to fit at least a portion of a residual limb of a user, wherein the rigid prosthetic socket comprises a first end, a second end, an inner circumference, the first end having an opening, the second end being substantially closed, and an inner surface having contours that substantially mimic contours of the residual limb, wherein the rigid prosthetic socket has not been globally reduced in dimension;
 providing a flexible pre-socket;
 heating the flexible pre-socket to a temperature so that the flexible pre-socket becomes a formable flexible pre-socket;
 arranging at least a portion of the formable flexible pre-socket into the rigid prosthetic socket; and
 molding the formable flexible pre-socket onto the inner surface of the rigid prosthetic socket such that an outer circumference of the formable flexible pre-socket substantially follows the contours of the inner surface of the rigid prosthetic socket comprising:
 providing a sleeve;
 arranging the sleeve around at least a portion of the formable flexible pre-socket extending past the first end of the rigid prosthetic socket and the at least a portion of an upper region of the rigid prosthetic socket near the first end, wherein the second end of the rigid prosthetic socket has a base with a channel that extends through the base from an inside of the rigid prosthetic socket to an outside of the rigid prosthetic socket, connecting a vacuum source to the channel in the base, and wherein the molding of the formable flexible pre-socket onto the inner surface is aided with a vacuum pressure from the vacuum source.

29. A method of forming a flexible inner socket, comprising:
providing a prosthetic socket having an inner surface with contours that substantially mimic contours of a residual limb, wherein the prosthetic socket has not been globally reduced;
providing a pre-socket;
heating the pre-socket with a heat source to a temperature where the pre-socket becomes moldable;
arranging at least a portion of the heated pre-socket into the prosthetic socket; and
molding the heated pre-socket onto the inner surface with a vacuum pressure such that an outer circumference of the pre-socket substantially follows one or more of the contours of the inner surface of the prosthetic socket.

* * * * *